(12) United States Patent
Bard et al.

(10) Patent No.: US 10,455,834 B2
(45) Date of Patent: Oct. 29, 2019

(54) INSECT RESISTANT AND HERBICIDE TOLERANT SOYBEAN EVENT PDAB9582.816.15.1

(71) Applicant: DOW AGROSCIENCES LLC, Indianapolis, IN (US)

(72) Inventors: Nathan Bard, Edgerton, WI (US); Gregory A. Bradfisch, Carmel, IN (US); Yunxing Cory Cui, Carmel, IN (US); James E. Dripps, Carmel, IN (US); Thomas Hoffman, Zionsville, IN (US); Dayakar Pareddy, Carmel, IN (US); Dawn M. Parkhurst, Avon, IN (US); Sandra G. Toledo, West Lafayette, IN (US); Barry Wiggins, Westfield, IN (US); Ning Zhou, Zionsville, IN (US); Aaron T. Woosley, Fishers, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 683 days.

(21) Appl. No.: 14/410,762

(22) PCT Filed: Jun. 25, 2013

(86) PCT No.: PCT/US2013/047539
§ 371 (c)(1),
(2) Date: Dec. 23, 2014

(87) PCT Pub. No.: WO2014/004458
PCT Pub. Date: Jan. 3, 2014

(65) Prior Publication Data
US 2015/0335017 A1 Nov. 26, 2015

Related U.S. Application Data

(60) Provisional application No. 61/663,700, filed on Jun. 25, 2012.

(51) Int. Cl.
*C12N 15/82* (2006.01)
*A01N 43/16* (2006.01)
*A01H 5/10* (2018.01)

(52) U.S. Cl.
CPC ............ *A01N 43/16* (2013.01); *A01H 5/10* (2013.01); *C12N 15/8274* (2013.01); *C12N 15/8286* (2013.01); *Y02A 40/162* (2018.01)

(58) Field of Classification Search
CPC ............ C12Q 1/6895; C12N 15/8274; C12N 15/8286; C12N 15/8209; A01N 37/38; A01N 37/44; A01N 65/20
See application file for complete search history.

(56) References Cited

U.S. PATENT DOCUMENTS

| | | |
|---|---|---|
| 2009/0041887 A1 | 12/2009 | Resnessen et al. |
| 2011/0191900 A1 | 8/2011 | Ping et al. |

FOREIGN PATENT DOCUMENTS

| | | |
|---|---|---|
| JP | 2009525748 | 7/2009 |
| JP | 2009538153 | 11/2009 |

(Continued)

OTHER PUBLICATIONS

Gryson, Nicolas, et al. "Detection of DNA during the refining of soybean oil." Journal of the American Oil Chemists' Society 79.2 (2002): 171-174.*

(Continued)

*Primary Examiner* — Weihua Fan
(74) *Attorney, Agent, or Firm* — Barnes & Thornburg LLP

(57) ABSTRACT

Soybean event 9582.816.15.1 comprises genes encoding Cry1 F, Cry1 Ac (synpro), and PAT, affording insect resistance and herbicide tolerance to soybean crops containing the event, and enabling methods for crop protection and protection of stored products. Embodiments of the present (Continued)

The diagram depicts the primer locations for confirming the 5' and 3' border sequence of the soybean event pDAB9582.816.15.1.

disclosure relate to a new insect resistant and herbicide tolerant transgenic soybean transformation event, designated soybean event pDAB9582.816.15.1, comprising cry1F v3 (cry1F), cry1Ac synpro (cry1Ac) and pat v6 (pat), as described herein, inserted into a specific site within the genome of a soybean cell. Representative soybean seed has been deposited with American Type Culture Collection (ATCC) with the Accession No. ATCC Deposit No. PTA-12588. The DNA of soybean plants containing this event includes the junction/flanking sequences described herein that characterize the location of the inserted DNA within the soybean genome.

18 Claims, 3 Drawing Sheets

Specification includes a Sequence Listing.

(56) References Cited

FOREIGN PATENT DOCUMENTS

| RU | 2234531 | C2 | 8/2004 | | |
|---|---|---|---|---|---|
| WO | 0026371 | A1 | 5/2000 | | |
| WO | 2007140256 | A1 | 6/2007 | | |
| WO | 2007091277 | A2 | 8/2007 | | |
| WO | 2011063413 | A2 | 5/2011 | | |
| WO | 2011066384 | A1 | 6/2011 | | |
| WO | 2012075426 | A1 | 6/2012 | | |
| WO | 2012075429 | A1 | 6/2012 | | |
| WO | WO 2012/075426 | A1 * | 6/2012 | ............... | A01H 5/00 |
| WO | WO-2012075426 | A1 * | 6/2012 | ......... | C12N 15/8274 |
| WO | 2013016527 | A1 | 1/2013 | | |

OTHER PUBLICATIONS

Christou, Paul, et al. "Inheritance and expression of foreign genes in transgenic soybean plants." Proceedings of the National Academy of Sciences 86.19 (1989): 7500-7504.*

Crespo et al., "Cross-resistance and mechanism of resistance to Cry1Ab toxin from Bacillus thuringiensis in a field-derived strain of European corn borer, *Ostrinia nubilalis*", Journal of Invertebrate Pathology, (Apr. 29, 2011), vol. 107, pp. 185-192.

Putu Suparthana, "Development of generic, simple, high efficiency in planta transformation method," The Society for Bioscience and Bioengineering, Japan, 2007, 85(2): 57-62 (In Japanese).

* cited by examiner

Figure 1. is a plasmid Map of pDAB9582 containing the *cry1F* v3, *cry1Ac* and *pat* v6 expression cassette.
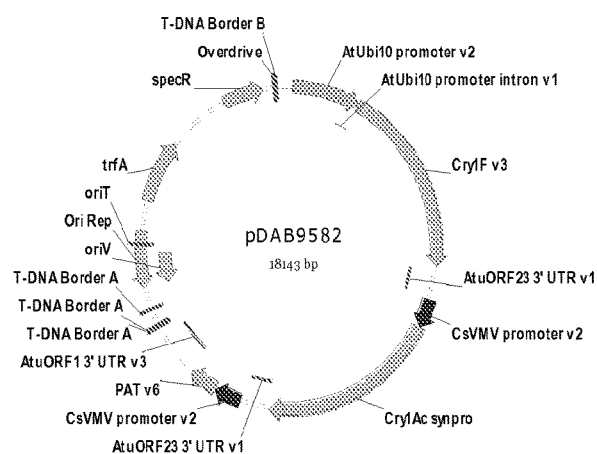

Figure 2. The diagram depicts the primer locations for confirming the 5' and 3' border sequence of the soybean event pDAB9582.816.15.1.
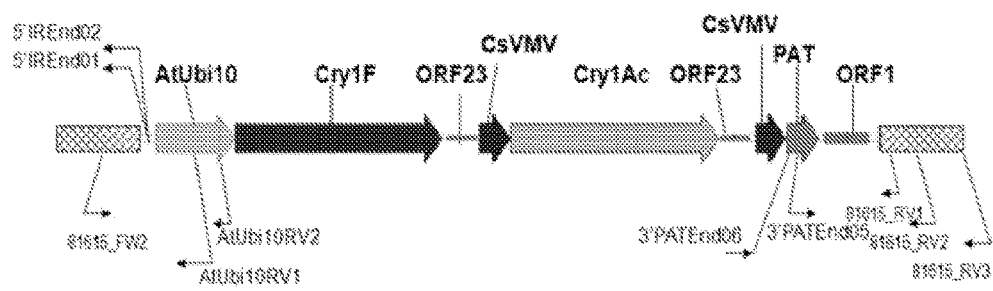

Figure 3. The diagram depicts the genomic sequence arrangement in soybean event pDAB9582.816.15.1
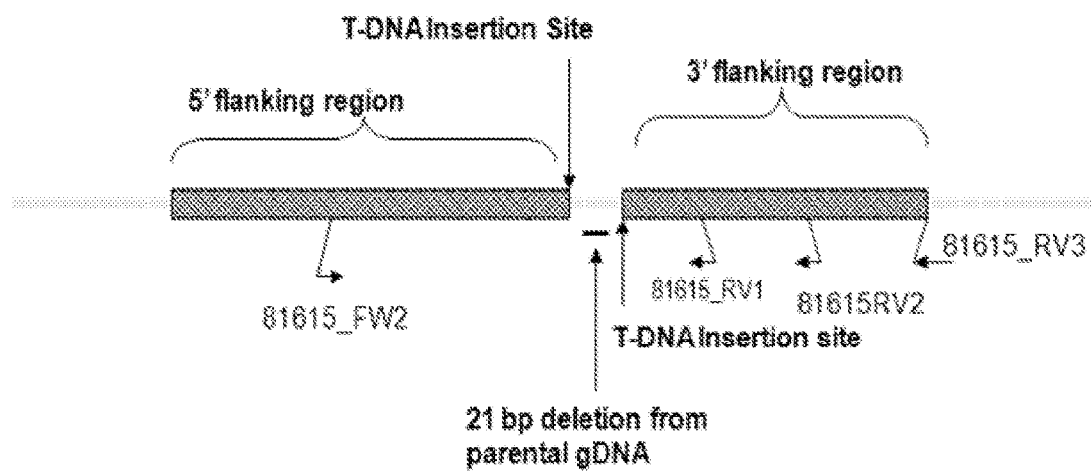

INSECT RESISTANT AND HERBICIDE TOLERANT SOYBEAN EVENT PDAB9582.816.15.1

CROSS-REFERENCE TO RELATED APPLICATIONS

This application is a U.S. National Phase filing of PCT/US2013/047539, filed Jun. 25, 2013, which claims the benefit of U.S. Provisional Application No. 61/663,700, filed Jun. 25, 2012. The disclosure therein is expressly incorporated entirely by reference.

BACKGROUND OF INVENTION

The genes encoding Cry1F and Cry1Ac synpro (Cry1Ac) are capable of imparting insect resistance, e.g. resistance to lepidopteran insects, to transgenic plants; and the gene encoding PAT (phosphinothricin acetyltransferase) is capable of imparting tolerance to the herbicide phoshpinothricin (glufosinate) to transgenic plants. PAT has been successfully expressed in soybean for use both as a selectable marker in producing insect resistant transgenic crops, and to impart commercial levels of tolerance to the herbicide glufosinate in transgenic plants.

The expression of transgenes in plants is known to be influenced by their location in the plant genome, perhaps due to chromatin structure (e.g., heterochromatin) or the proximity of transcriptional regulatory elements (e.g., enhancers) close to the integration site (Weising et al., *Ann. Rev. Genet* 22:421-477, 1988). At the same time the presence of the transgene at different locations in the genome will influence the overall phenotype of the plant in different ways. For this reason, it is often necessary to screen a large number of transgenic events in order to identify a specific transgenic event characterized by optimal expression of an introduced gene of interest. For example, it has been observed in plants and in other organisms that there may be a wide variation in levels of expression of an introduced gene among events. There may also be differences in spatial or temporal patterns of expression, for example, differences in the relative expression of a transgene in various plant tissues, that may not correspond to the patterns expected from transcriptional regulatory elements present in the introduced gene construct. For this reason, it is common to produce hundreds to thousands of different events and screen those events for a single event that has desired transgene expression levels and patterns for commercial purposes. An event that has desired levels or patterns of transgene expression is useful for introgressing the transgene into other genetic backgrounds by sexual outcrossing using conventional breeding methods. Progeny of such crosses maintain the transgene expression characteristics of the original transformant. This strategy is used to ensure reliable gene expression in a number of varieties that are well adapted to local growing conditions.

It is desirable to be able to detect the presence of a particular event in order to determine whether progeny of a sexual cross contain a transgene or group of transgenes of interest. In addition, a method for detecting a particular event would be helpful for complying with regulations requiring the pre-market approval and labeling of foods derived from recombinant crop plants, for example, or for use in environmental monitoring, monitoring traits in crops in the field, or monitoring products derived from a crop harvest, as well as for use in ensuring compliance of parties subject to regulatory or contractual terms.

It is possible to detect the presence of a transgenic event by any nucleic acid detection method known in the art including, but not limited to, the polymerase chain reaction (PCR) or DNA hybridization using nucleic acid probes. These detection methods generally focus on frequently used genetic elements, such as promoters, terminators, marker genes, etc., because for many DNA constructs, the coding region is interchangeable. As a result, such methods may not be useful for discriminating between different events, particularly those produced using the same DNA construct or very similar constructs unless the DNA sequence of the flanking DNA adjacent to the inserted heterologous DNA is known. For example, an event-specific PCR assay is described in United States Patent Application 2006/0070139 for maize event DAS-59122-7. It would be desirable to have a simple and discriminative method for the identification of soybean event pDAB9582.816.15.1.

BRIEF SUMMARY OF THE INVENTION

Embodiments of the present disclosure relate to a new insect resistant and herbicide tolerant transgenic soybean transformation event, designated soybean event pDAB9582.816.15.1, comprising cry1F v3 (cry1F), cry1Ac synpro (cry1Ac) and pat v6 (pat), as described herein, inserted into a specific site within the genome of a soybean cell. Representative soybean seed has been deposited with American Type Culture Collection (ATCC) with the Accession No. identified in paragraph[0033]. The DNA of soybean plants containing this event includes the junction/flanking sequences described herein that characterize the location of the inserted DNA within the soybean genome. SEQ ID NO:1 and SEQ ID NO:2 are diagnostic for soybean event pDAB9582.816.15.1. More particularly, sequences surrounding the junctions at by 1273/1274 of SEQ ID NO:1, and by 175/176 and 316/317 of SEQ ID NO:2 are diagnostic for soybean event pDAB9582.816.15.1. Paragraph[0012] below describes examples of sequences comprising these junctions that are characteristic of DNA of soybeans containing soybean event pDAB9582.816.15.1.

In one embodiment, the disclosure provides a soybean plant, or part thereof, that is resistant to *Pseudoplusia includens* (soybean looper) and that has a genome comprising one or more sequences selected from the group consisting of bp 1258-1288 of SEQ ID NO:1; bp 1223-1323 of SEQ ID NO:1; bp 1173-1373 of SEQ ID NO:1; bp 1073-1473 of SEQ ID NO:1; bp 160-190 of SEQ ID NO:2; bp 125-225 of SEQ ID NO:2; and by 75-275 of SEQ ID NO:2, and compliments thereof. In another embodiment, the disclosure provides seed of such plants.

In another embodiment, the disclosure provides a method of controlling insects that comprises exposing insects to insect resistant soybean plants, wherein the soybean plants have a genome that contains one or more sequences selected from the group consisting of bp1258-1288 of SEQ ID NO:1; bp 1223-1323 of SEQ ID NO:1; by 1173-1373 of SEQ ID NO:1; bp 1073-1473 of SEQ ID NO:1; bp 160-190 of SEQ ID NO:2; bp 125-225 of SEQ ID NO:2; and bp 75-275 of SEQ ID NO:2, and compliments thereof which are characteristic of the presence of soybean event pDAB9582.816.15.1, to thereby control the insects. Presence of the cry1F v3 (cry1F) and cry1Ac synpro (cry1Ac) genes in soybean event pDAB9582.816.15.1 imparts resistance to, for example, *Pseudoplusia includens* (soybean looper), *Anticarsia gemmatalis* (velvetbean caterpillar), *Epinotia aporema*, *Omoides indicatus*, *Rachiplusia nu*, *Spodoptera frugiperda*, *Spodoptera cosmoides*, *Spodoptera erida-* nia, *Heliothis virescens*, *Heliocoverpa zea*, *Spilosoma virginica* and *Elasmopalpus lignosellus*.

In another embodiment, the disclosure provides a method of controlling weeds in a soybean crop that comprises applying glufosinate herbicide to the soybean crop, said soybean crop comprising soybean plants that have a genome containing one or more sequence selected from the group consisting of bp 1258-1288 of SEQ ID NO:1; bp 1223-1323 of SEQ ID NO:1; bp 1173-1373 of SEQ ID NO:1; bp 1073-1473 of SEQ ID NO:1; bp 160-190 of SEQ ID NO:2; bp 125-225 of SEQ ID NO:2; and bp 75-275 of SEQ ID NO:2, and compliments thereof, which are diagnostic for the presence of soybean event pDAB9582.816.15.1. Presence of the pat gene in soybean event pDAB9582.816.15.1 imparts tolerance to glufosinate herbicide.

In another embodiment, the disclosure provides a method of detecting soybean event pDAB9582.816.15.1 in a sample comprising soybean DNA, said method comprising:
(a) contacting said sample with a first primer at least 10 bp in length that selectively binds to a flanking sequence within by 1-1273 of SEQ ID NO:1 or the complement thereof, and a second primer at least 10 bp in length that selectively binds to an insert sequence within by 1274-1577 of SEQ ID NO:1 or the complement thereof; and assaying for an amplicon generated between said primers; or
(b) contacting said sample with a first primer at least 10 bp in length that selectively binds to an insert sequence within by 1-175 of SEQ ID NO:2 or the complement thereof, and a second primer at least 10 bp in length that selectively binds to flanking sequence within by 176-1687 of SEQ ID NO:2 or the complement thereof; and
(c) assaying for an amplicon generated between said primers.

In another embodiment, the disclosure provides a method of detecting soybean event pDAB9582.816.15.1 comprising:
a) contacting said sample with a first primer that selectively binds to a flanking sequence selected from the group consisting of bp 1-1273 of SEQ ID NO:1 and bp 176-1687 of SEQ ID NO:2, and compliments thereof; and a second primer that selectively binds to SEQ ID NO:3, or the compliment thereof;
b) subjecting said sample to polymerase chain reaction; and
c) assaying for an amplicon generated between said primers.

In another embodiment the disclosure provides a method of breeding a soybean plant comprising: crossing a first plant with a second soybean plant to produce a third soybean plant, said first plant comprising DNA comprising one or more sequence selected from the group consisting of bp 1258-1288 of SEQ ID NO:1; bp 1223-1323 of SEQ ID NO:1; bp 1173-1373 of SEQ ID NO:1; bp 1073-1473 of SEQ ID NO:1; bp 160-190 of SEQ ID NO:2; bp 125-225 of SEQ ID NO:2; and bp 75-275 of SEQ ID NO:2, and compliments thereof; and assaying said third soybean plant for presence of DNA comprising one or more sequences selected from the group consisting of bp1258-1288 of SEQ ID NO:1; bp 1223-1323 of SEQ ID NO:1; bp 1173-1373 of SEQ ID NO:1; bp 1073-1473 of SEQ ID NO:1; bp 160-190 of SEQ ID NO:2; bp 125-225 of SEQ ID NO:2; and bp 75-275 of SEQ ID NO:2, and compliments thereof.

In another embodiment the disclosure provides an isolated DNA molecule that is diagnostic for soybean event pDAB9582.816.15.1. Such molecules include, in addition to SEQ ID NOS: 1 and 2, molecules at least 25 bp in length comprising bp 1273-1274 of SEQ ID NO:1 and at least 10 bp of SEQ ID NO:1 in each direction from the by 1273/1274 junction; amplicons at least 25 bp in length comprising 175-176 of SEQ ID NO:2 and at least 10 bp of SEQ ID NO:2 in each direction from the by 175/176 junction. Examples are bp1258-1288 of SEQ ID NO:1; bp 1223-1323 of SEQ ID NO:1; bp 1173-1373 of SEQ ID NO:1; bp 1073-1473 of SEQ ID NO:1; bp 160-190 of SEQ ID NO:2; bp 125-225 of SEQ ID NO:2; and bp 75-275 of SEQ ID NO:2, and compliments thereof.

In another embodiment the disclosure provides a method of controlling pests in soybean grain, seed, or seed meal which comprises including soybean event pDAB9-582.816.15.1 in said grain, seed, or seed meal as demonstrated by said grain, seed, or seed meal comprising DNA comprising one or more sequence selected from the group consisting of bp1258-1288 of SEQ ID NO:1; bp 1223-1323 of SEQ ID NO:1; bp 1173-1373 of SEQ ID NO:1; bp 1073-1473 of SEQ ID NO:1; bp 160-190 of SEQ ID NO:2; bp 125-225 of SEQ ID NO:2; and bp 75-275 of SEQ ID NO:2, and compliments thereof.

Embodiments of the disclosure also includes soybean plant cells and plant parts including, but are not limited to, pollen, ovule, flowers, shoots, roots, and leaves, and nuclei of vegetative cells, pollen cells, seed and seed meal, and egg cells, that contain soybean event pDAB 9582.816.15.1.

In some embodiments, soybean event pDAB 9582.816.15.1 can be combined with other traits, including, for example, other herbicide tolerance gene(s) and/or insect-inhibitory proteins and transcription regulatory sequences (i.e. RNA interference, dsRNA, transcription factors, etc). The additional traits may be stacked into the plant genome via plant breeding, re-transformation of the transgenic plant containing soybean event pDAB 9582.816.15.1, or addition of new traits through targeted integration via homologous recombination.

Other embodiments include the excision of polynucleotide sequences which comprise soybean event pDAB9582.816.15.1, including for example, the pat gene expression cassette. Upon excision of a polynucleotide sequence, the modified event may be re-targeted at a specific chromosomal site wherein additional polynucleotide sequences are stacked with soybean event pDAB95-82.816.15.1.

In one embodiment, the present disclosure encompasses a soybean chromosomal target site located on chromosome 03 between the flanking sequences set forth in SEQ ID NOS:1 and 2.

In one embodiment, the present disclosure encompasses a method of making a transgenic soybean plant comprising inserting a heterologous nucleic acid at a position on chromosome 03 between the genomic sequences set forth in SEQ ID NOS:1 and 2, i.e. between bp 1-1273 of SEQ ID NO:1 and bp 176-1687 of SEQ ID NO:2.

Additionally, embodiments of the disclosure also provide assays for detecting the presence of the subject event in a sample (of soybeans, for example). The assays can be based on the DNA sequence of the recombinant construct, inserted into the soybean genome, and on the genomic sequences flanking the insertion site. Kits and conditions useful in conducting the assays are also provided.

Embodiments of the disclosure also relate in part to the cloning and analysis of the DNA sequences of the border regions resulting from insertion of T-DNA from pDAB9582 in transgenic soybean lines. These sequences are unique. Based on the insert and junction sequences, event-specific primers can be and were generated. PCR analysis demonstrated that these events can be identified by analysis of the PCR amplicons generated with these event-specific primer sets. Thus, these and other related procedures can be used to uniquely identify soybean lines comprising the event of the subject disclosure.

An embodiment provides a method of controlling insects that comprises exposing insects to insect resistant soybean plants, said soybean plants comprising DNA that comprises a sequence selected from the group consisting of bp 1258-1288 of SEQ ID NO:1; bp 1223-1323 of SEQ ID NO:1; bp 1173-1373 of SEQ ID NO:1; bp 1073-1473 of SEQ ID NO:1; bp 160-190 of SEQ ID NO:2; bp 125-225 of SEQ ID NO:2; and bp 75-275 of SEQ ID NO:2 said sequence being diagnostic for the presence of soybean event pDAB9582.816.15.1, to thereby control the insects.

An embodiment provides a method of controlling *Pseudoplusia includens, Anticarsia gemmatalis,* or *Spodoptera frugiperda* that comprises exposing *Pseudoplusia includens, Anticarsia gemmatalis, Heliothis virescens,* or *Spodoptera frugiperda* to insect resistant soybean plants, said soybean plants comprising DNA that comprises a sequence selected from the group consisting of bp 1258-1288 of SEQ ID NO:1; bp 1223-1323 of SEQ ID NO:1; bp 1173-1373 of SEQ ID NO:1; bp 1073-1473 of SEQ ID NO:1; bp 160-190 of SEQ ID NO:2; bp 125-225 of SEQ ID NO:2; and bp 75-275 of SEQ ID NO:2 said sequence being diagnostic for the presence of soybean event pDAB9582.816.15.1, to thereby control the insects.

An embodiment provides a method of controlling weeds in a soybean crop that comprises applying glufosinate herbicide to the soybean crop, said soybean crop comprising soybean plants comprising a DNA that comprises a sequence selected from the group consisting of sequence selected from the group consisting of bp 1258-1288 of SEQ ID NO:1; bp 1223-1323 of SEQ ID NO:1; bp 1173-1373 of SEQ ID NO:1; bp 1073-1473 of SEQ ID NO:1; bp 160-190 of SEQ ID NO:2; bp 125-225 of SEQ ID NO:2; and by 75-275 of SEQ ID NO:2 said sequence being diagnostic for the presence of soybean event pDAB9582.816.15.1.

An embodiment provides an isolated DNA sequence comprising one or more sequences selected from the group consisting of bp 1258-1288 of SEQ ID NO:1; by 1223-1323 of SEQ ID NO:1; bp 1173-1373 of SEQ ID NO:1; bp 1073-1473 of SEQ ID NO:1; bp 160-190 of SEQ ID NO:2; bp 125-225 of SEQ ID NO:2; and bp 75-275 of SEQ ID NO:2.

An embodiment provides a method of breeding a soybean plant comprising: crossing a first plant with a second soybean plant to produce a third soybean plant, said first plant comprising DNA comprising one or more sequences selected from the group consisting of 1258-1288 of SEQ ID NO:1; bp 1223-1323 of SEQ ID NO:1; bp 1173-1373 of SEQ ID NO:1; bp 1073-1473 of SEQ ID NO:1; bp 160-190 of SEQ ID NO:2; bp 125-225 of SEQ ID NO:2; and bp 75-275 of SEQ ID NO:2 and compliments thereof; and assaying said third soybean plant for presence of DNA comprising one or more sequences selected from the group consisting of 1258-1288 of SEQ ID NO:1; bp 1223-1323 of SEQ ID NO:1; bp 1173-1373 of SEQ ID NO:1; bp 1073-1473 of SEQ ID NO:1; by 160-190 of SEQ ID NO:2; bp 125-225 of SEQ ID NO:2; and bp 75-275 of SEQ ID NO:2, and compliments thereof.

An embodiment provides an isolated DNA molecule comprising a junction sequence comprising at least one sequence selected from the group consisting of by 1258-1288 of SEQ ID NO:1; bp 1223-1323 of SEQ ID NO:1; bp 1173-1373 of SEQ ID NO:1; bp 1073-1473 of SEQ ID NO:1; bp 160-190 of SEQ ID NO:2; bp 125-225 of SEQ ID NO:2; and bp 75-275 of SEQ ID NO:2, and compliments thereof. An embodiment provides a soybean plant, or part thereof, that is resistant to *Pseudoplusia includens* (soybean looper) and comprises DNA having at least one nucleotide sequence selected from the group consisting of bp 1258-1288 of SEQ ID NO:1; bp 1223-1323 of SEQ ID NO:1; bp 1173-1373 of SEQ ID NO:1; bp 1073-1473 of SEQ ID NO:1; bp 160-190 of SEQ ID NO:2; bp 125-225 of SEQ ID NO:2; and bp 75-275 of SEQ ID NO:2, and compliments thereof.

An embodiment provides a composition derived from the soybean plant, or parts thereof, wherein said composition is a commodity product selected from the group consisting of soybean meal, flour, protein concentrate, and oil.

An embodiment provides a method of controlling pests in soybean grain, seed, meal, or flour which comprises including soybean event pDAB9582.816.15.1 in said grain, seed, meal, or flour as demonstrated by said grain, seed, meal, or flour comprising DNA comprising one or more sequence selected from the group consisting of bp1258-1288 of SEQ ID NO:1; bp 1223-1323 of SEQ ID NO:1; bp 1173-1373 of SEQ ID NO:1; by 1073-1473 of SEQ ID NO:1; bp 160-190 of SEQ ID NO:2; bp 125-225 of SEQ ID NO:2; and bp 75-275 of SEQ ID NO:2, and compliments thereof.

An embodiment provides a soybean seed comprising in its genome a DNA sequence selected from the group consisting of bp1258-1288 of SEQ ID NO:1; bp 1223-1323 of SEQ ID NO:1; bp 1173-1373 of SEQ ID NO:1; bp 1073-1473 of SEQ ID NO:1; by 160-190 of SEQ ID NO:2; bp 125-225 of SEQ ID NO:2; and bp 75-275 of SEQ ID NO:2, and compliments thereof. A further embodiment provides a soybean seed comprising in its genome cry1F, cry1Ac, and pat of soybean event pDAB9582.816.15.1 and having representative soybean seed deposited with American Type Culture Collection under Accession No. PTA-12588. A further embodiment provides a soybean plant produced by growing a soybean seed of either of these two embodiments. A further embodiment provides a soybean seed produced by this soybean plant, wherein said seed comprises in its genome the cry1F, cry 1Ac, and pat genes of soybean event pDAB9582.816.15.1 that are present in a soybean seed deposited with American Type Culture Collection under Accession No. PTA-12588. A further embodiment provides a part of this soybean plant, wherein said part is selected from the group consisting of pollen, ovule, flowers, shoots, roots, and leaves, and said part comprises said event. A further embodiment provides a composition derived from the soybean plant or a part thereof, wherein said composition is a commodity product selected from the group consisting of soybean meal, flour, and oil.

In a further embodiment, the soybean plant comprises a DNA sequence having at least 95% sequence identity with SEQ ID NO:14. An embodiment provides a progeny soybean plant of the plant of the above embodiment, wherein said plant exhibits tolerance to a glufosinate herbicide, and said tolerance is due to expression of a protein encoded in said event or said genome.

A further embodiment provides a soybean seed comprising a genome comprising a DNA sequence having at least 95% sequence identity with SEQ ID NO:14. A further embodiment provides a plant produced by growing this soybean seed.

An embodiment provides a transgenic soybean plant or part thereof comprising soybean event pDAB9582.816.15.1, wherein representative soybean seeds comprising soybean event pDAB9582.816.15.1 have been deposited with American Type Culture Collection under Accession No. PTA-12588.

Seed Deposit

As part of this disclosure at least 2500 seeds of a soybean line comprising soybean event pDAB9582.816.15.1 have been deposited and made available to the public without restriction (but subject to patent rights), with the American Type Culture Collection (ATCC), 10801 University Boulevard, Manassas, Va., 20110. The deposit, designated as ATCC Deposit No. PTA-12588, was made on behalf of Dow AgroSciences LLC on 23 Feb. 2012. This deposit was made and will be maintained in accordance with and under the terms of the Budapest Treaty with respect to seed deposits for the purposes of patent procedure.

BRIEF DESCRIPTION OF THE SEQUENCES

SEQ ID NO:1 is the 5' DNA flanking border sequence for soybean event pDAB9582.816.15.1. Nucleotides 1-1273 are genomic sequence. Nucleotides 1274-1577 are insert sequence.

SEQ ID NO:2 is the 3' DNA flanking border sequence for soybean event pDAB9582.816.15.1. Nucleotides 1-175 are insert sequence. Nucleotides 176-316 are a rearranged sequence from pDAB9582. Nucleotides 317-1687 are genomic sequence.

SEQ ID NO:3 is the T-strand DNA sequence of pDAB9582, which is annotated below in Table 1.

SEQ ID NO:4 is oligonucleotide primer 81615_FW2 for confirmation of 5' border genomic DNA.

SEQ ID NO:5 is oligonucleotide primer 81516_RV1 for confirmation of 3' border genomic DNA.

SEQ ID NO:6 is oligonucleotide primer 81516_RV2 for confirmation of 3' border genomic DNA.

SEQ ID NO:7 is oligonucleotide 81516_RV3 for confirmation of 3' border genomic DNA.

SEQ ID NO:8 is oligonucleotide primer 5'IREnd-01 for confirmation of 5' border genomic DNA.

SEQ ID NO:9 is oligonucleotide primer 5'IREnd-02 for confirmation of 5' border genomic DNA.

SEQ ID NO:10 is oligonucleotide primer AtUbi10RV1 for confirmation of 5' border genomic DNA.

SEQ ID NO:11 is oligonucleotide primer AtUbi10RV2 for confirmation of 5' border genomic DNA.

SEQ ID NO:12 is oligonucleotide primer 3'PATEnd05 for confirmation of 3' border genomic DNA.

SEQ ID NO:13 is oligonucleotide primer 3'PATEnd06 for confirmation of 3' border genomic DNA.

SEQ ID NO:14 is the expected sequence of soybean event pDAB9582.816.15.1. Including the 5' genomic flanking sequence, pDAB9582 T-strand insert, and 3' genomic flanking sequence.

BRIEF DESCRIPTION OF THE FIGURES

FIG. 1 is a plasmid map of pDAB9582 containing the cry1F v3, cry1Ac synpro and pat v6 gene expression cassettes.

FIG. 2 depicts the primer locations for confirming the 5' and 3' border sequence of the soybean event pDAB9582.816.15.1.

FIG. 3 depicts the genomic sequence arrangement in soybean event pDAB9582.816.15.1

DETAILED DESCRIPTION OF THE INVENTION

Both ends of event soybean event pDAB9582.816.15.1 insertion have been sequenced and characterized. Event specific assays were developed. The event has also been mapped onto the soybean genome (soybean chromosome 03). The event can be introgressed into further elite lines.

As alluded to above in the Background section, the introduction and integration of a transgene into a plant genome involves some random events (hence the name "event" for a given insertion that is expressed). That is, with many transformation techniques such as *Agrobacterium* transformation, the biolistic transformation (i.e. gene gun), and silicon carbide mediated transformation (i.e. WHISKERS™), it is unpredictable where in the genome a transgene will become inserted. Thus, identifying the flanking plant genomic DNA on both sides of the insert can be important for identifying a plant that has a given insertion event. For example, PCR primers can be designed that generate a PCR amplicon across the junction region of the insert and the host genome. This PCR amplicon can be used to identify a unique or distinct type of insertion event.

Definitions and examples are provided herein to help describe embodiments of the present disclosure and to guide those of ordinary skill in the art to practice those embodiments. Unless otherwise noted, terms are to be understood according to conventional usage by those of ordinary skill in the relevant art. The nomenclature for DNA bases as set forth at 37 CFR § 1.822 is used.

As used herein, the term "progeny" denotes the offspring of any generation of a parent plant which comprises soybean event pDAB9582.816.15.1.

A transgenic "event" is produced by transformation of plant cells with heterologous DNA, i.e., a nucleic acid construct that includes the transgenes of interest, regeneration of a population of plants resulting from the insertion of the transgene into the genome of the plant, and selection of a particular plant characterized by insertion into a particular genome location. The term "event" refers to the original transformant and progeny of the transformant that include the heterologous DNA. The term "event" also refers to progeny produced by a sexual outcross between the transformant and another variety, the progeny of which includes the genomic/transgene DNA. Even after repeated backcrossing to a recurrent parent, the inserted transgene DNA and flanking genomic DNA (genomic/transgene DNA) from the transformed parent is present in the progeny of the cross at the same chromosomal location. The term "event" also refers to DNA from the original transformant and progeny, thereof, comprising the inserted DNA and flanking genomic sequence immediately adjacent to the inserted DNA, which would be expected to be transferred to a progeny that receives inserted DNA including the transgene of interest as the result of a sexual cross of one parental line that includes the inserted DNA (e.g., the original transformant and progeny resulting from selfing) and a parental line that does not contain the inserted DNA.

A "junction sequence" or "border sequence" spans the point at which DNA inserted into the genome is linked to DNA from the soybean native genome flanking the insertion point, the identification or detection of one or the other junction sequences in a plant's genetic material being sufficient to be diagnostic for the event. Included are the DNA sequences that span the insertions in herein-described soybean events and similar lengths of flanking DNA. Specific examples of such diagnostic sequences are provided herein; however, other sequences that overlap the junctions of the insertions, or the junctions of the insertions and the genomic sequence, are also diagnostic and could be used in accordance with embodiments of the disclosure.

Embodiments of the disclosure relate in part to event identification using such flanking, junction, and insert sequences. Related PCR primers and amplicons are included in embodiments of the disclosure. In accordance with embodiments of the subject disclosure, PCR analysis methods using amplicons that span across inserted DNA and its borders can be used to detect or identify commercialized transgenic soybean varieties or lines derived from the subject proprietary transgenic soybean lines.

The flanking/junction sequences are diagnostic for soybean event pDAB9582.816.15.1. Based on these sequences, event-specific primers were generated. PCR analysis demonstrated that these soybean lines can be identified in different soybean genotypes by analysis of the PCR amplicons generated with these event-specific primer sets. Thus, these and other related procedures can be used to uniquely identify these soybean lines. The sequences identified herein are unique.

Detection techniques of embodiments of the subject disclosure are especially useful in conjunction with plant breeding, to determine which progeny plants comprise a given event, after a parent plant comprising an event of interest is crossed with another plant line in an effort to impart one or more additional traits of interest in the progeny. These PCR analysis methods benefit soybean breeding programs as well as quality control, especially for commercialized transgenic soybean seeds. PCR detection kits for these transgenic soybean lines can also now be made and used. This is also beneficial for product registration and product stewardship.

Furthermore, flanking soybean/genomic sequences can be used to specifically identify the genomic location of each insert. This information can be used to make molecular marker systems specific to each event. These can be used for accelerated breeding strategies and to establish linkage data.

Still further, the flanking sequence information can be used to study and characterize transgene integration processes, genomic integration site characteristics, event sorting, stability of transgenes and their flanking sequences, and gene expression (especially related to gene silencing, transgene methylation patterns, position effects, and potential expression-related elements such as MARS [matrix attachment regions], and the like).

In light of all the subject disclosure, it should be clear that embodiments of the subject disclosure include seeds available under the ATCC Deposit No. identified in paragraph [0033]. Embodiments of the disclosure also include a herbicide-tolerant soybean plant grown from a seed deposited with the ATCC Deposit No. identified in paragraph[0033]. Embodiments of the disclosure also include parts of said plant, such as leaves, tissue samples, seeds produced by said plant, pollen, and the like (wherein these parts of the plant comprise cry1F, cry1Ac, pat, and SEQ ID NOS: 1 and 2).

Still further, embodiments of the disclosure also include descendant and/or progeny plants of plants grown from the deposited seed, preferably a herbicide-resistant soybean plant wherein said plant has a genome comprising a detectable wild-type junction/flanking sequence as described herein. As used herein, the term "soybean" means *Glycine max* and includes all varieties thereof that can be bred with a soybean plant.

This disclosure further includes processes of making crosses using a plant of the subject disclosure as at least one parent. For example, the subject disclosure includes an $F_1$ hybrid plant having as one or both parents any of the plants exemplified herein. Also within the subject disclosure is seed produced by such $F_1$ hybrids of the subject disclosure.

This disclosure includes a method for producing an $F_1$ hybrid seed by crossing an exemplified plant with a different (e.g. in-bred parent) plant and harvesting the resultant hybrid seed. The subject disclosure includes an exemplified plant that is either a female parent or a male parent. Characteristics of the resulting plants may be improved by careful consideration of the parent plants.

An insect resistant/glufonsinate-tolerant soybean plant of the subject disclosure can be bred by first sexually crossing a first parental soybean plant consisting of a soybean plant grown from seed of any one of the lines referred to herein, and a second parental soybean plant, thereby producing a plurality of first progeny plants; then selecting a first progeny plant that is resistant to glufosinate; selfing the first progeny plant, thereby producing a plurality of second progeny plants; and then selecting from the second progeny plants a plant that is resistant to glufosinate. These steps can further include the back-crossing of the first progeny plant or the second progeny plant to the second parental soybean plant or a third parental soybean plant. A soybean crop comprising soybean seeds of the subject disclosure, or progeny thereof, can then be planted.

It is also to be understood that two different transgenic plants can also be mated to produce offspring that contain two independently segregating, added, exogenous genes. Selfing of appropriate progeny can produce plants that are homozygous for both added, exogenous genes. Back-crossing to a parental plant and out-crossing with a non-transgenic plant are also contemplated, as is vegetative propagation. Other breeding methods commonly used for different traits and crops are known in the art. Backcross breeding has been used to transfer genes for a simply inherited, highly heritable trait into a desirable homozygous cultivar or inbred line, which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

Likewise an insect resistant/glufosinate-tolerant soybean plant of an embodiment of the disclosure can be transformed with additional transgenes using methods known in the art. Transformation techniques such as *Agrobacterium* transformation, the biolistic transformation (i.e. gene gun), and silicon carbide mediated transformation (i.e. WHISKERS™), can be used to introduced additional trangene(s) into the genome of soybean event pDAB9582.816.15.1. Selection and characterization of transgenic plants containing the newly inserted transgenes can be completed to identify plants which contain a stable integrant of the novel transgene in addition to cry1F, cry1Ac, pat genes of embodiments of the disclosure.

The DNA molecules of embodiments of the present disclosure can be used as molecular markers in a marker assisted breeding (MAB) method. DNA molecules of embodiments of the present disclosure can be used in methods (such as, AFLP markers, RFLP markers, RAPD markers, SNPs, and SSRs) that identify genetically linked agronomically useful traits, as is known in the art. The insect resistance and herbicide-tolerance traits can be tracked in the progeny of a cross with a soybean plant of embodiments of the subject disclosure (or progeny thereof and any other soybean cultivar or variety) using the MAB methods. The DNA molecules are markers for this trait, and MAB methods that are well known in the art can be used to track the herbicide tolerance trait(s) in soybean plants where at least one soybean line of embodiments of the subject disclosure, or progeny thereof, was a parent or ancestor. The methods of embodiments of the present disclosure can be used to identify any soybean variety having the subject event.

Embodiments of the subject disclosure include a method of producing an insect resistant/herbicide-tolerant soybean plant wherein said method comprises breeding with a plant that is embodied within the subject disclosure. More specifically, said methods can comprise crossing two plants embodied within the subject disclosure, or one plant of embodied within the subject disclosure and any other plant. Preferred methods further comprise selecting progeny of said cross by analyzing said progeny for an event detectable in accordance with an embodiment of the subject disclosure and favorable varietal performance (e.g. yield). For example, embodiments of the subject disclosure can be used to track the subject event through breeding cycles with plants comprising other desirable traits, such as agronomic traits, disease tolerance or resistance, nematode tolerance or resistance and maturity date. Plants comprising the subject event and the desired trait can be detected, identified, selected, and quickly used in further rounds of breeding, for example. The subject event/trait can also be combined through breeding, and tracked according to embodiments of the subject disclosure, with further insect resistant trait(s) and/or with further herbicide tolerance traits. Embodiments of the latter are plants comprising the subject event combined with the cry1F and cry1Ac genes, which confer resistance to Lepidopteran species, which include; *Pseudoplusia includens* (soybean looper), *Anticarsia gemmatalis* (velvetbean caterpillar), *Epinotia aporema, Omiodes indicata, Rachiplusia nu, Spodoptera frugiperda, Spodoptera cosmoides, Spodoptera eridania, Heliothis virescens, Heliocoverpa zea, Spilosoma virginica* and *Elasmopalpus lignosellus*.

Thus, embodiments of the subject disclosure can be combined with, for example, traits encoding glyphosate resistance (e.g., resistant plant or bacterial EPSPS, GOX, GAT), glufosinate resistance (e.g., dsm-2, bar), acetolactate synthase (ALS)-inhibiting herbicide resistance (e.g., imidazolinones [such as imazethapyr], sulfonylureas, triazolopyrimidine sulfonanilide, pyrmidinylthiobenzoates, and other chemistries [Csr1, SurA, et al.]), bromoxynil resistance (e.g., Bxn), resistance to inhibitors of HPPD (4-hydroxlphenyl-pyruvate-dioxygenase) enzyme, resistance to inhibitors of phytoene desaturase (PDS), resistance to photosystem II inhibiting herbicides (e.g., psbA), resistance to photosystem I inhibiting herbicides, resistance to protoporphyrinogen oxidase IX (PPO)-inhibiting herbicides (e.g., PPO-1), resistance to phenylurea herbicides (e.g., CYP76B1), dicamba-degrading enzymes (see, e.g., US 20030135879), and others could be stacked alone or in multiple combinations to provide the ability to effectively control or prevent weed shifts and/or resistance to any herbicide of the aforementioned classes.

Additionally, soybean event pDAB9582.816.15.1 can be combined with one or more additional input (e.g., insect resistance, pathogen resistance, or stress tolerance, et al.) or output (e.g., increased yield, improved oil profile, improved fiber quality, et al.) traits. Thus, embodiments of the subject disclosure can be used to provide a complete agronomic package of improved crop quality with the ability to flexibly and cost effectively control any number of agronomic pests.

Methods to integrate a polynucleotide sequence within a specific chromosomal site of a plant cell via homologous recombination have been described within the art. For instance, site specific integration as described in US Patent Application Publication No. 2009/0111188 A1, herein incorporated by reference, describes the use of recombinases or integrases to mediate the introduction of a donor polynucleotide sequence into a chromosomal target. In addition, International Patent Application No. WO 2008/021207, herein incorporated by reference, describes zinc finger mediated-homologous recombination to integrate one or more donor polynucleotide sequences within specific locations of the genome. The use of recombinases such as FLP/FRT as described in U.S. Pat. No. 6,720,475, herein incorporated by reference, or CRE/LOX as described in U.S. Pat. No. 5,658,772, herein incorporated by reference, can be utilized to integrate a polynucleotide sequence into a specific chromosomal site. Finally the use of meganucleases for targeting donor polynucleotides into a specific chromosomal location was described in Puchta et al., *PNAS USA* 93 (1996) pp. 5055-5060).

Other methods for site specific integration within plant cells are generally known and applicable (Kumar et al., *Trends in Plant Sci*. 6(4) (2001) pp. 155-159). Furthermore, site-specific recombination systems which have been identified in several prokaryotic and lower eukaryotic organisms may be applied to use in plants. Examples of such systems include, but are not limited to: the R/RS recombinase system from the pSR1 plasmid of the yeast *Zygosaccharomyces rouxii* (Araki et al. (1985) J. Mol. Biol. 182: 191-203), and the Gin/Gix system of phage Mu (Maeser and Kahlmann (1991) Mol. Gen. Genet. 230: 170-176).

In some embodiments of the present disclosure, it is desirable to integrate or stack a new transgene(s) in proximity to an existing transgenic event. The transgenic event can be considered a preferred genomic locus which was selected based on unique characteristics such as single insertion site, normal Mendelian segregation and stable expression, and a superior combination of efficacy, including herbicide tolerance and agronomic performance in and across multiple environmental locations. Progeny plants comprising the integrated transgenes should maintain the transgene expression characteristics of the existing transformants. Moreover, progeny plants comprising the integrated event can utilize previously developed assays for the detection and confirmation of the, as the genomic flanking sequences and chromosomal location of progeny plants comprising the event are already identified. Finally, the integration of a new transgene into a specific chromosomal location which is closely linked to an existing transgene would expedite the introgression of the transgenes into other genetic backgrounds by sexual out-crossing using conventional breeding methods.

In some embodiments of the present disclosure, it is desirable to excise polynucleotide sequences from a transgenic event. For instance, transgene excision as described in US Patent Application Publication No. 2011/0191877, herein incorporated by reference, describes the use of zinc finger nucleases to remove a polynucleotide sequence, consisting of a gene expression cassette, from a chromosomally integrated transgenic event. The polynucleotide sequence which is removed can be a selectable marker. Upon excision and removal of a polynucleotide sequence the modified transgenic event can be retargeted by the insertion of a polynucleotide sequence. The excision of a polynucleotide sequence and subsequent retargeting of the modified transgenic event provides advantages such as re-use of a selectable marker or the ability to overcome unintended changes to the plant transcriptome which results from the expression of specific genes.

Disclosed herein is a specific site on chromosome 03 in the soybean genome that can be used for the insertion of heterologous nucleic acids. Thus, embodiments of the subject disclosure provide methods to introduce heterologous nucleic acids of interest into this pre-established target site or in the vicinity of this target site. Embodiments of the subject disclosure also encompass a soybean seed and/or a soybean plant comprising any heterologous nucleotide sequence inserted at the disclosed target site or in the general vicinity of such site. One option to accomplish such targeted integration is to excise and/or substitute a different insert in place of the pat expression cassette exemplified herein. In this general regard, targeted homologous recombination, for example and without limitation, can be used in accordance with embodiments of the subject disclosure.

As used herein gene, event or trait "stacking" refers to the combining of desired traits into one transgenic line. Plant breeders stack transgenic traits by making crosses between parents that each have a desired trait and then identifying offspring that have both of these desired traits. Another way to stack genes is by transferring two or more genes into the cell nucleus of a plant at the same time during transformation. Another way to stack genes is by re-transforming a transgenic plant with another gene of interest. For example, gene stacking can be used to combine two or more different traits, including for example, two or more different insect traits, insect resistance trait(s) and disease resistance trait(s), two or more herbicide resistance traits, and/or insect resistance trait(s) and herbicide resistant trait(s). The use of a selectable marker in addition to a gene of interest can also be considered gene stacking.

"Homologous recombination" refers to a reaction between any pair of nucleotide sequences having corresponding sites containing a similar nucleotide sequence through which the two nucleotide sequences can interact (recombine) to form a new, recombinant DNA sequence. The sites of similar nucleotide sequence are each referred to herein as a "homology sequence." Generally, the frequency of homologous recombination increases as the length of the homology sequence increases. Thus, while homologous recombination can occur between two nucleotide sequences that are less than identical, the recombination frequency (or efficiency) declines as the divergence between the two sequences increases. Recombination may be accomplished using one homology sequence on each of the donor and target molecules, thereby generating a "single-crossover" recombination product. Alternatively, two homology sequences may be placed on each of the target and donor nucleotide sequences. Recombination between two homology sequences on the donor with two homology sequences on the target generates a "double-crossover" recombination product. If the homology sequences on the donor molecule flank a sequence that is to be manipulated (e.g., a sequence of interest), the double-crossover recombination with the target molecule will result in a recombination product wherein the sequence of interest replaces a DNA sequence that was originally between the homology sequences on the target molecule. The exchange of DNA sequence between the target and donor through a double-crossover recombination event is termed "sequence replacement."

A preferred plant, or a seed, of embodiments of the subject disclosure comprises in its genome operative cry1F, cry1Ac synpro and pat nucleotide sequences, as identified herein, together with at least 20-500 or more contiguous flanking nucleotides on both sides of the insert, as identified herein. Unless indicated otherwise, reference to flanking sequences refers to those identified with respect to SEQ ID NOS: 1 and 2. All or part of these flanking sequences could be expected to be transferred to progeny that receive the inserted DNA as a result of a sexual cross of a parental line that includes the event.

Embodiments of the subject disclosure include tissue cultures of regenerable cells of a plant of an embodiment of the subject disclosure. Also included is a plant regenerated from such tissue culture, particularly where said plant is capable of expressing all the morphological and physiological properties of an exemplified variety. Preferred plants of embodiments of the subject disclosure have all the physiological and morphological characteristics of a plant grown from the deposited seed. Embodiments of this disclosure further comprise progeny of such seed and seed possessing the quality traits of interest.

As used herein, a "line" is a group of plants that display little or no genetic variation between individuals for at least one trait. Such lines may be created by several generations of self-pollination and selection, or vegetative propagation from a single parent using tissue or cell culture techniques.

As used herein, the terms "cultivar" and "variety" are synonymous and refer to a line which is used for commercial production.

"Stability" or "stable" means that with respect to the given component, the component is maintained from generation to generation and, preferably, for at least three generations.

"Commercial Utility" is defined as having good plant vigor and high fertility, such that the crop can be produced by farmers using conventional farming equipment, and the oil with the described components can be extracted from the seed using conventional crushing and extraction equipment.

"Agronomically elite" means that a line has desirable agronomic characteristics such as yield, maturity, disease resistance, and the like, in addition to the insect resistance and herbicide tolerance due to the subject event(s). Any and all of these agronomic characteristics and data points can be used to identify such plants, either as a point or at either end or both ends of a range of characteristics used to define such plants.

As one skilled in the art will recognize in light of this disclosure, preferred embodiments of detection kits, for example, can include probes and/or primers directed to and/or comprising "junction sequences" or "transition sequences" (where the soybean genomic flanking sequence meets the insert sequence). For example, this includes polynucleotide probes, primers, and/or amplicons designed to identify one or both junction sequences (where the insert meets the flanking sequence). One common design is to have one primer that hybridizes in the flanking region, and one primer that hybridizes in the insert. Such primers are often each about at least ~15 residues in length. With this arrangement, the primers can be used to generate/amplify a detectable amplicon that indicates the presence of an event of an embodiment of the subject disclosure. These primers can be used to generate an amplicon that spans (and includes) a junction sequence as indicated above.

The primer(s) "touching down" in the flanking sequence is typically not designed to hybridize beyond about 1200 bases or so beyond the junction. Thus, typical flanking primers would be designed to comprise at least 15 residues of either strand within 1200 bases into the flanking sequences from the beginning of the insert. That is, primers comprising a sequence of an appropriate size from (or hybridizing to) base pairs 1 to 1273 of SEQ ID NO:1 and/or base pairs 176 to 1687 of SEQ ID NO:2 are within the scope of embodiments of the subject disclosure. Insert primers can likewise be designed anywhere on the insert, but base pairs 1273 to 1873 and 13058 to 13658 of SEQ ID NO:14, can be used, for example, non-exclusively for such primer design.

One skilled in the art will also recognize that primers and probes can be designed to hybridize, under a range of standard hybridization and/or PCR conditions wherein the primer or probe is not perfectly complementary to the exemplified sequence. That is, some degree of mismatch or degeneracy can be tolerated. For an approximately 20 nucleotide primer, for example, typically one or two or so nucleotides do not need to bind with the opposite strand if the mismatched base is internal or on the end of the primer that is opposite the amplicon. Various appropriate hybridization conditions are provided below. Synthetic nucleotide analogs, such as inosine, can also be used in probes. Peptide nucleic acid (PNA) probes, as well as DNA and RNA probes, can also be used. What is important is that such probes and primers are diagnostic for (able to uniquely identify and distinguish) the presence of an event of an embodiment of the subject disclosure.

It should be noted that errors in PCR amplification can occur which might result in minor sequencing errors, for example. That is, unless otherwise indicated, the sequences listed herein were determined by generating long amplicons from soybean genomic DNAs, and then cloning and sequencing the amplicons. It is not unusual to find slight differences and minor discrepancies in sequences generated and determined in this manner, given the many rounds of amplification that are necessary to generate enough amplicon for sequencing from genomic DNAs. One skilled in the art should recognize and be put on notice that any adjustments needed due to these types of common sequencing errors or discrepancies are within the scope of embodiments of the subject disclosure.

It should also be noted that it is not uncommon for some genomic sequence to be deleted, for example, when a sequence is inserted during the creation of an event. Thus, some differences can also appear between the subject flanking sequences and genomic sequences listed in GENBANK, for example.

Components of the DNA sequence "insert" are illustrated in the Figures and are discussed in more detail below in the Examples. The DNA polynucleotide sequences of these components, or fragments thereof, can be used as DNA primers or probes in the methods of embodiments of the present disclosure.

In some embodiments of the disclosure, compositions and methods are provided for detecting the presence of the transgene/genomic insertion region, in plants and seeds and the like, from a soybean plant. DNA sequences are provided that comprise the subject 5' transgene/genomic insertion region junction sequence provided herein (between base pairs 1 to 1273 of SEQ ID NO:1 and 1 to 1273 of SEQ ID NO:14), segments thereof, and complements of the exemplified sequences and any segments thereof. DNA sequences are provided that comprise the subject 3' transgene/genomic insertion region junction sequence provided herein (between base pairs 176 to 1687 of SEQ ID NO:2 and 13659 to 15170 of SEQ ID NO:14), segments thereof, and complements of the exemplified sequences and any segments thereof. The insertion region junction sequence spans the junction between heterologous DNA inserted into the genome and the DNA from the soybean cell flanking the insertion site. Such sequences can be diagnostic for the given event.

Based on these insert and border sequences, event-specific primers can be generated. PCR analysis demonstrated that soybean lines of embodiments of the subject disclosure can be identified in different soybean genotypes by analysis of the PCR amplicons generated with these event-specific primer sets. These and other related procedures can be used to uniquely identify soybean lines comprising soybean event pDAB9582.816.15.1. Thus, PCR amplicons derived from such primer pairs are unique and can be used to identify these soybean lines.

In some embodiments, DNA sequences that comprise a contiguous fragment of the novel transgene/genomic insertion region are an aspect of this disclosure. Included are DNA sequences that comprise a sufficient length of polynucleotides of transgene insert sequence and a sufficient length of polynucleotides of soybean genomic sequence from one or more of the three aforementioned soybean plants and/or sequences that are useful as primer sequences for the production of an amplicon product diagnostic for one or more of these soybean plants.

Related embodiments pertain to DNA sequences that comprise at least 10, 11, 12, 13, 14, 15, 16, 17, 18, 19, 20, 21, 22, 23, 24, 25, or more contiguous nucleotides of a transgene portion of a DNA sequence identified herein (such as SEQ ID NO:1 and segments thereof), or complements thereof, and a similar length of flanking soybean DNA sequence from these sequences, or complements thereof. Such sequences are useful as DNA primers in DNA amplification methods. The amplicons produced using these primers are diagnostic for any of the soybean events referred to herein. Therefore, embodiments of the disclosure also include the amplicons produced by such DNA primers.

Embodiments of this disclosure also include methods of detecting the presence of DNA, in a sample, that corresponds to the soybean event referred to herein. Such methods can comprise: (a) contacting the sample comprising DNA with a primer set that, when used in a nucleic acid amplification reaction with DNA from at least one of these soybean events, produces an amplicon that is diagnostic for said event(s); (b) performing a nucleic acid amplification reaction, thereby producing the amplicon; and (c) detecting the amplicon.

Further detection methods of embodiments of the subject disclosure include a method of detecting the presence of a DNA, in a sample, corresponding to said event, wherein said method comprises: (a) contacting the sample comprising DNA with a probe that hybridizes under stringent hybridization conditions with DNA from said soybean events and which does not hybridize under the stringent hybridization conditions with a control soybean plant (non-event-of-interest DNA); (b) subjecting the sample and probe to stringent hybridization conditions; and (c) detecting hybridization of the probe to the DNA.

In still further embodiments, the subject disclosure includes methods of producing a soybean plant comprising soybean event pDAB9582.816.15.1 of an embodiment of the subject disclosure, wherein said method comprises the steps of: (a) sexually crossing a first parental soybean line (comprising an expression cassette of an embodiment of the present disclosure, which confers glufosinate tolerance to plants of said line) and a second parental soybean line (that lacks this herbicide tolerance trait) thereby producing a plurality of progeny plants; and (b) selecting a progeny plant by the use of molecular markers. Such methods may optionally comprise the further step of back-crossing the progeny plant to the second parental soybean line to producing a true-breeding soybean plant that comprises the insect resistant and glufosinate tolerant trait.

According to another aspect of the disclosure, methods of determining the zygosity of progeny of a cross with said event is provided. Said methods can comprise contacting a sample, comprising soybean DNA, with a primer set of an embodiment of the subject disclosure. Said primers, when used in a nucleic-acid amplification reaction with genomic DNA from said soybean events, produce a first amplicon that is diagnostic for said soybean events. Such methods further comprise performing a nucleic acid amplification reaction, thereby producing the first amplicon; detecting the first amplicon; and contacting the sample comprising soybean DNA with a second primer set (said second primer set, when used in a nucleic-acid amplification reaction with genomic DNA from soybean plants, produces a second amplicon comprising an endogenous sequence of the native soybean genomic DNA that does not contain the polynucleotide sequence of said event); and performing a nucleic acid amplification reaction, thereby producing the second amplicon. The methods further comprise detecting the second amplicon, and comparing the first and second amplicons in a sample, wherein the presence of both amplicons indicates the zygosity of the transgene insertion.

DNA detection kits can be developed using the compositions disclosed herein and methods well known in the art of DNA detection. The kits are useful for identification of the subject soybean event DNA in a sample and can be applied to methods for breeding soybean plants containing this DNA. The kits contain DNA sequences complementary to the amplicons, for example, disclosed herein, or to DNA sequences complementary to DNA contained in the transgene genetic elements of the subject events. These DNA sequences can be used in DNA amplification reactions or as probes in a DNA hybridization method. The kits may also contain the reagents and materials necessary for the performance of the detection method.

A "probe" is an isolated nucleic acid molecule to which is attached a conventional detectable label or reporter molecule (such as a radioactive isotope, ligand, chemiluminescent agent, or enzyme). Such a probe can hybridize to a strand of a target nucleic acid, in the case of embodiments of the present disclosure, to a strand of genomic DNA from one of said soybean events, whether from a soybean plant or from a sample that includes DNA from the event. Probes in accordance with embodiments of the present disclosure include not only deoxyribonucleic or ribonucleic acids but also polyamides and other probe materials that bind specifically to a target DNA sequence and can be used to detect the presence of that target DNA sequence.

"Primers" are isolated/synthesized nucleic acids that are annealed to a target DNA strand by nucleic acid hybridization to form a hybrid between the primer and the target DNA strand, then extended along the target DNA strand by a polymerase, e.g., a DNA polymerase. Primer pairs of embodiments of the present disclosure refer to their use for amplification of a target nucleic acid sequence, e.g., by the polymerase chain reaction (PCR) or other conventional nucleic-acid amplification methods.

Probes and primers are generally 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, or 1000, or 2000, or 5000 polynucleotides or more in length. Such probes and primers hybridize specifically to a target sequence under stringent hybridization conditions. Preferably, probes and primers in accordance with embodiments of the present disclosure have complete sequence similarity with the target sequence, although probes differing from the target sequence and that retain the ability to hybridize to target sequences may be designed by conventional methods.

Methods for preparing and using probes and primers are described, for example, in Molecular Cloning: A Laboratory Manual, 2nd ed., vol. 1-3, ed. Sambrook et al., Cold Spring Harbor Laboratory Press, Cold Spring Harbor, N.Y., 1989. PCR-primer pairs can be derived from a known sequence, for example, by using computer programs intended for that purpose.

Primers and probes based on the flanking DNA and insert sequences disclosed herein can be used to confirm (and, if necessary, to correct) the disclosed sequences by conventional methods, e.g., by re-cloning and sequencing such sequences.

The nucleic acid probes and primers of embodiments of the present disclosure hybridize under stringent conditions to a target DNA sequence. Any conventional nucleic acid hybridization or amplification method can be used to identify the presence of DNA from a transgenic event in a sample. Nucleic acid molecules or fragments thereof are capable of specifically hybridizing to other nucleic acid molecules under certain circumstances. As used herein, two nucleic acid molecules are said to be capable of specifically hybridizing to one another if the two molecules are capable of forming an anti-parallel, double-stranded nucleic acid structure. A nucleic acid molecule is said to be the "complement" of another nucleic acid molecule if they exhibit complete complementarity. As used herein, molecules are said to exhibit "complete complementarity" when every nucleotide of one of the molecules is complementary to a nucleotide of the other. Molecules that exhibit complete complementarity will generally hybridize to one another with sufficient stability to permit them to remain annealed to one another under conventional "high-stringency" conditions. Conventional high-stringency conditions are described by Sambrook et al., 1989.

Two molecules are said to exhibit "minimal complementarity" if they can hybridize to one another with sufficient stability to permit them to remain annealed to one another under at least conventional "low-stringency" conditions. Conventional low-stringency conditions are described by Sambrook et al., 1989. In order for a nucleic acid molecule to serve as a primer or probe it need only exhibit minimal complementarity of sequence to be able to form a stable double-stranded structure under the particular solvent and salt concentrations employed.

The term "stringent condition" or "stringency conditions" is functionally defined with regard to the hybridization of a nucleic-acid probe to a target nucleic acid (i.e., to a particular nucleic-acid sequence of interest) by the specific hybridization procedure discussed in Sambrook et al., 1989, at 9.52-9.55. See also, Sambrook et al., 1989 at 9.47-9.52 and 9.56-9.58.

Depending on the application envisioned, one can use varying conditions of stringent conditions or polynucleotide sequence degeneracy of a probe or primer to achieve varying degrees of selectivity of hybridization towards the target sequence. For applications requiring high selectivity, one will typically employ relatively stringent conditions for hybridization of one polynucleotide sequence with a second polynucleotide sequence, e.g., one will select relatively low salt and/or high temperature conditions, such as provided by about 0.02 M to about 0.15 M NaCl at temperatures of about 50° C. to about 70° C. Stringent conditions, for example, could involve washing the hybridization filter at least twice with high-stringency wash buffer (0.2×SSC, 0.1% SDS, 65° C.). Appropriate stringency conditions which promote DNA hybridization, for example, 6.0× sodium chloride/sodium citrate (SSC) at about 45° C., followed by a wash of 2.0×SSC at 50° C. are known to those skilled in the art. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed. Such selective conditions tolerate little, if any, mismatch between the probe and the template or target strand. Detection of DNA sequences via hybridization is well-known to those of skill in the art, and the teachings of U.S. Pat. Nos. 4,965,188 and 5,176,995 are exemplary of the methods of hybridization analyses.

In a particularly preferred embodiment, a nucleic acid of an embodiment of the present disclosure will specifically hybridize to one or more of the primers (or amplicons or other sequences) exemplified or suggested herein, including complements and fragments thereof, under high stringency conditions. In one aspect of the present disclosure, a marker nucleic acid molecule of an embodiment of the present disclosure has the nucleic acid sequence as set forth herein in one of the exemplified sequences, or complements and/or fragments thereof.

In another aspect of the present disclosure, a marker nucleic acid molecule of an embodiment of the present disclosure shares between 80% and 100% or 90% and 100% sequence identity with such nucleic acid sequences. In a further aspect of the present disclosure, a marker nucleic acid molecule of an embodiment of the present disclosure shares between 95% and 100% sequence identity with such sequence. Such sequences may be used as markers in plant breeding methods to identify the progeny of genetic crosses. The hybridization of the probe to the target DNA molecule can be detected by any number of methods known to those skilled in the art; these can include, but are not limited to, fluorescent tags, radioactive tags, antibody based tags, and chemiluminescent tags.

Regarding the amplification of a target nucleic acid sequence (e.g., by PCR) using a particular amplification primer pair, "stringent conditions" are conditions that permit the primer pair to hybridize only to the target nucleic-acid sequence to which a primer having the corresponding wild-type sequence (or its complement) would bind and preferably to produce a unique amplification product, the amplicon.

The term "specific for (a target sequence)" indicates that a probe or primer hybridizes under stringent hybridization conditions only to the target sequence in a sample comprising the target sequence.

As used herein, "amplified DNA" or "amplicon" refers to the product of nucleic-acid amplification of a target nucleic acid sequence that is part of a nucleic acid template. For example, to determine whether the soybean plant resulting from a sexual cross contains transgenic event genomic DNA from the soybean plant of an embodiment of the present disclosure, DNA extracted from a soybean plant tissue sample may be subjected to nucleic acid amplification method using a primer pair that includes a primer derived from flanking sequence in the genome of the plant adjacent to the insertion site of inserted heterologous DNA, and a second primer derived from the inserted heterologous DNA to produce an amplicon that is diagnostic for the presence of the event DNA. The amplicon is of a length and has a sequence that is also diagnostic for the event. The amplicon may range in length from the combined length of the primer pairs plus one nucleotide base pair, and/or the combined length of the primer pairs plus about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, or 500, 750, 1000, 1250, 1500, 1750, 2000, or more nucleotide base pairs (plus or minus any of the increments listed above). Alternatively, a primer pair can be derived from flanking sequence on both sides of the inserted DNA so as to produce an amplicon that includes the entire insert nucleotide sequence. A member of a primer pair derived from the plant genomic sequence may be located a distance from the inserted DNA sequence. This distance can range from one nucleotide base pair up to about twenty thousand nucleotide base pairs. The use of the term "amplicon" specifically excludes primer dimers that may be formed in the DNA thermal amplification reaction.

Nucleic-acid amplification can be accomplished by any of the various nucleic-acid amplification methods known in the art, including the polymerase chain reaction (PCR). A variety of amplification methods are known in the art and are described, inter alia, in U.S. Pat. Nos. 4,683,195 and 4,683,202. PCR amplification methods have been developed to amplify up to 22 kb of genomic DNA. These methods as well as other methods known in the art of DNA amplification may be used in the practice of embodiments of the present disclosure. The sequence of the heterologous transgene DNA insert or flanking genomic sequence from a subject soybean event can be verified (and corrected if necessary) by amplifying such sequences from the event using primers derived from the sequences provided herein followed by standard DNA sequencing of the PCR amplicon or of the cloned DNA.

The amplicon produced by these methods may be detected by a plurality of techniques. Agarose gel electrophoresis and staining with ethidium bromide is a common well-known method of detecting DNA amplicons. Another such method is Genetic Bit Analysis, where an DNA oligonucleotide is designed which overlaps both the adjacent flanking genomic DNA sequence and the inserted DNA sequence. The oligonucleotide is immobilized in wells of a microwell plate. Following PCR of the region of interest (using one primer in the inserted sequence and one in the adjacent flanking genomic sequence), a single-stranded PCR product can be hybridized to the immobilized oligonucleotide and serve as a template for a single base extension reaction using a DNA polymerase and labeled ddNTPs specific for the expected next base. Analysis of a bound product can be completed via quantitating the amount of fluorescent signal. A fluorescent signal indicates presence of the insert/flanking sequence due to successful amplification, hybridization, and single base extension.

Another method is the Pyrosequencing technique as described by Winge (Innov. Pharma. Tech. 00:18-24, 2000). In this method an oligonucleotide is designed that overlaps the adjacent genomic DNA and insert DNA junction. The oligonucleotide is designed to hybridize to single-stranded PCR product from the region of interest (one primer in the inserted sequence and one in the flanking genomic sequence) and incubated in the presence of a DNA polymerase, ATP, sulfurylase, luciferase, apyrase, adenosine 5' phosphosulfate and luciferin. DNTPs are added individually and the incorporation results in a light signal that is measured. A light signal indicates the presence of the transgene insert/flanking sequence due to successful amplification, hybridization, and single or multi-base extension.

Fluorescence Polarization is another method that can be used to detect an amplicon of an embodiment of the present disclosure. Following this method, an oligonucleotide is designed which overlaps the genomic flanking and inserted DNA junction. The oligonucleotide is hybridized to the single-stranded PCR product from the region of interest (one primer in the inserted DNA and one in the flanking genomic DNA sequence) and incubated in the presence of a DNA polymerase and a fluorescent-labeled ddNTP. Single base extension results in incorporation of the ddNTP. Incorporation of the fluorescently labeled ddNTP can be measured as a change in polarization using a fluorometer. A change in polarization indicates the presence of the transgene insert/flanking sequence due to successful amplification, hybridization, and single base extension.

TAQMAN® (PE Applied Biosystems, Foster City, Calif.) is a method of detecting and quantifying the presence of a DNA sequence. Briefly, a FRET oligonucleotide probe is designed that overlaps the genomic flanking and insert DNA junction. The FRET probe and PCR primers (one primer in the insert DNA sequence and one in the flanking genomic sequence) are cycled in the presence of a thermostable polymerase and dNTPs. During specific amplification, the Taq DNA polymerase proofreading mechanism releases the fluorescent moiety away from the quenching moiety on the FRET probe. A fluorescent signal indicates the presence of the flanking/transgene insert sequence due to successful amplification and hybridization.

Molecular Beacons have been described for use in polynucleotide sequence detection. Briefly, a FRET oligonucleotide probe is designed that overlaps the flanking genomic and insert DNA junction. The unique structure of the FRET probe results in it containing secondary structure that keeps the fluorescent and quenching moieties in close proximity. The FRET probe and PCR primers (one primer in the insert DNA sequence and one in the flanking genomic sequence) are cycled in the presence of a thermostable polymerase and dNTPs. Following successful PCR amplification, hybridization of the FRET probe to the target sequence results in the removal of the probe secondary structure and spatial separation of the fluorescent and quenching moieties. A fluorescent signal results. A fluorescent signal indicates the presence of the flanking genomic/transgene insert sequence due to successful amplification and hybridization.

Having disclosed a location in the soybean genome that is excellent for an insertion, embodiments of the subject disclosure also comprise a soybean seed and/or a soybean plant comprising at least one non-soybean event pDAB9582.816.15.1 insert in the general vicinity of this genomic location. One option is to substitute a different insert in place of the one from soybean event pDAB9582.816.15.1 exemplified herein. In general, targeted homologous recombination, for example, is employed in particular embodiments. This type of technology is the subject of, for example, WO 03/080809 A2 and the corresponding published U.S. application (US 20030232410). Thus, embodiments of the subject disclosure include plants and plant cells comprising a heterologous insert (in place of or with multi-copies of the cry1F, cry1Ac, or pat genes), flanked by all or a recognizable part of the flanking sequences identified herein (bp 1-1273 of SEQ ID NO:1 and bp 176-1687 of SEQ ID NO:2). An additional copy (or additional copies) of a cry1F, cry1Ac, or pat could also be targeted for insertion in this/these manner(s).

All patents, patent applications, provisional applications, and publications referred to or cited herein are incorporated by reference in their entirety to the extent they are not inconsistent with the explicit teachings of this specification. The following examples are included to illustrate procedures for practicing embodiments of the disclosure and to demonstrate certain preferred embodiments of the disclosure. These examples should not be construed as limiting. It should be appreciated by those of skill in the art that the techniques disclosed in the following examples represent specific approaches used to illustrate preferred modes for its practice. However, those of skill in the art should, in light of the present disclosure, appreciate that many changes can be made in these specific embodiments while still obtaining like or similar results without departing from the spirit and scope of the disclosure. Unless otherwise indicated, all percentages are by weight and all solvent mixture proportions are by volume unless otherwise noted.

The following abbreviations are used unless otherwise indicated.
bp base pair
° C. degrees Celsius
DNA deoxyribonucleic acid
EDTA ethylenediaminetetraacetic acid
kb kilobase
μg microgram
μL microliter
mL milliliter
M molar mass
PCR polymerase chain reaction
PTU plant transcription unit or expression cassette
SDS sodium dodecyl sulfate
SSC a buffer solution containing a mixture of sodium chloride and sodium citrate, pH 7.0
TBE a buffer solution containing a mixture of Tris base, boric acid and EDTA, pH 8.3.

EXAMPLES

Example 1: Transformation and Selection of the Cry1F, Cry1Ac and PAT Soybean Event pDAB9582.816.15.1

Transgenic soybean (*Glycine max*) containing the soybean event pDAB9582.816.15.1 was generated through *Agrobacterium*-mediated transformation of soybean cotyledonary node explants. The disarmed *Agrobacterium* strain EHA101 (Hood et al., 1993), carrying the binary vector pDAB9582 (FIG. 1) containing the selectable marker, pat v6, and the genes of interest, cry1F v3 and cry1Ac synpro, within the T-strand DNA region, was used to initiate transformation. The T-strand DNA sequence for pDAB9582 is given in SEQ ID NO:3, which is annotated below in Table 1.

TABLE 1

Gene elements located on pDAB9582.

| bp (SEQ ID NO: 3) | Construct Element | Reference |
|---|---|---|
| 272-1593 | AtUbi10 Promoter | Callis, et al., (1990) *J. Biol. Chem.*, 265: 12486-12493 |

TABLE 1-continued

Gene elements located on pDAB9582.

| bp (SEQ ID NO: 3) | Construct Element | Reference |
|---|---|---|
| 1602-5048 | Cry1F | Referenced above |
| 5151-5607 | ORF23 3'UTR | U.S. Pat. No. 5,428,147 |
| 5671-6187 | CsVMV Promoter | Verdaguer et al., (1996) *Plant Mol. Biol.*, 31: 1129-1139 |
| 6197-9667 | Cry 1AC | Referenced above |
| 9701-10157 | ORF23 3'UTR | U.S. Pat. No. 5,428,147 |
| 10272-10788 | CsVMV Promoter | Verdaguer et al., (1996) *Plant Mol. Biol.*, 31: 1129-1139 |
| 10796-11347 | PAT | Wohlleben et al., (1988) *Gene* 70: 25-37 |
| 11450-12153 | ORF1 3'UTR | Huang et al., (1990) *J. Bacteriol.* 172: 1814-1822 |

*Agrobacterium*-mediated transformation was carried out using a modified procedure of Zeng et al. (2004). Briefly, soybean seeds (cv Maverick) were germinated on basal media and cotyledonary nodes were isolated and infected with *Agrobacterium*. Shoot initiation, shoot elongation, and rooting media were supplemented with cefotaxime, timentin and vancomycin for removal of *Agrobacterium*. Glufosinate selection was employed to inhibit the growth of non-transformed shoots. Selected shoots were transferred to rooting medium for root development and then transferred to soil mix for acclimatization of plantlets.

Terminal leaflets of selected plantlets were leaf painted with glufosinate to screen for putative transformants. The screened plantlets were transferred to the greenhouse, allowed to acclimate and then leaf-painted with glufosinate to reconfirm tolerance and deemed to be putative transformants. The screened plants were sampled and molecular analyses for the confirmation of the selectable marker gene and/or the gene of interest were carried out. $T_0$ plants were allowed to self fertilize in the greenhouse to give rise to $T_1$ seed.

This event, soybean event pDAB9582.816.15.1, was generated from an independent transformed isolate. The $T_1$ plants were backcrossed and introgressed into elite varieties over subsequent generations. The event was selected based on its unique characteristics such as single insertion site, normal Mendelian segregation, stable expression, and a superior combination of efficacy, including insect resistance, herbicide tolerance and agronomic performance. The following examples contain the data which were used to characterize soybean event pDAB9582.816.15.1.

Example 2: Characterization of Protein Expression in Soybean Event pDAB9582.816.15.1

The biochemical properties of the recombinant Cry1F, Cry1Ac, and PAT proteins expressed in soybean event pDAB9582.816.15.1 were characterized. Quantitative enzyme-linked immunosorbent assay (ELISA) is a biochemical assay known within the art that can be used to characterize the biochemical properties of the proteins and confirm expression of these proteins in soybean event pDAB9582.816.15.1.

Example 2.1: Expression of the PAT, Cry1F, and Cry1Ac Protein in Plant Tissues

Samples of soybean tissues were isolated from the test plants and prepared for expression analysis. The PAT protein was extracted from soybean plant tissues with a phosphate buffered saline solution containing the detergent Tween-20 (PBST) containing 0.5% Bovine Serum Albumin (BSA). The plant tissue was centrifuged; the aqueous supernatant was collected, diluted with appropriate buffer as necessary, and analyzed using an PAT ELISA kit in a sandwich format. The kit was used following the manufacturer's suggested protocol (Envirologix, Portland, Me.). This assay measured the concentrations of expressed PAT protein.

The Cry1F protein was extracted from soybean plant tissues with a phosphate buffered saline solution containing the detergent Tween-20 (PBST). The plant tissue was centrifuged; the aqueous supernatant was collected, diluted with appropriate buffer as necessary, and analyzed using an Cry1F ELISA kit in a sandwich format. The kit was used following the manufacturer's suggested protocol (Strategic Diagnostics Inc., Newark, Del.). This assay measured the concentrations of expressed Cry1F protein.

The Cry1Ac protein was extracted from soybean plant tissues with a phosphate buffered saline solution containing the detergent Tween-20 (PBST) containing 0.5% Bovine Serum Albumin (BSA). The plant tissue was centrifuged; the aqueous supernatant was collected, diluted with appropriate buffer as necessary, and analyzed using an Cry1Ac ELISA kit in a sandwich format. The kit was used following the manufacturer's suggested protocol (Strategic Diagnostics Inc., Newark, Del.). This assay measured the concentrations of expressed Cry1Ac protein.

Detection analysis was performed to investigate the expression stability and inheritability both vertically (between generations) and horizontally (between lineages within a generation) in soybean event pDAB9582.816.15.1.

Example 2.2: Expression of Cry1F, Cry1Ac and PAT Proteins in Plant Tissues

Levels of Cry1F, Cry1Ac and PAT proteins were determined in Soybean event pDAB9582.816.15.1 using the protocols described above. The soluble, extractable proteins were measured using a quantitative enzyme-linked immunosorbent assay (ELISA) method from soybean leaf tissue. From $T_2$ to $T_6$ generations soybean event pDAB9582.816.15.1, expression was stable (not segregating) and consistent across all lineages. Table 2 lists the mean expression level of the transgenic proteins in soybean event pDAB9582.816.15.1.

TABLE 2

Mean expression level of different transgenic proteins in soybean event pDAB9582.816.15.1.
Expression Level of Different Proteins (ng/cm$^2$)

| Event | Cry1F | Cry1Ac | PAT |
|---|---|---|---|
| Soybean event pDAB9285.816.15.1 | 89 | 18.6 | 9.9 |

Example 3: Cloning and Characterization of DNA Sequence in the Insert and the Flanking Border Regions of Soybean Event pDAB9582.816.15.1

To characterize and describe the genomic insertion site, the sequence of the flanking genomic T-DNA border regions of soybean event pDAB9582.816.15.1 were determined. Genomic sequence of soybean event pDAB9582.816.15.1 was confirmed, comprising 1273 bp of 5' flanking border sequence (SEQ ID NO:1) and 1371 bp of 3' flanking border sequence (SEQ ID NO:2). PCR amplification based on the soybean event pDAB9582.816.15.1 border sequences validated that the border regions were of soybean origin and that the junction regions are unique sequences for soybean event pDAB9582.816.15.1. The junction regions could be used for event-specific identification of soybean event pDAB9582.816.15.1. In addition, the T-strand insertion site was characterized by amplifying a genomic fragment corresponding to the region of the identified flanking border sequences from the genome of untransformed soybean. Comparison of soybean event pDAB9582.816.15.1 with the untransformed genomic sequence revealed that a deletion of about 21 bp from the original locus resulted during the T-strand integration. Overall, the characterization of the insert and border sequence of soybean event pDAB9582.816.15.1 indicated that an intact copy of the T-strand from pDAB9582 was present in the soybean genome.

TABLE 3

List of primers and their sequences used in the confirmation of soybean genomic DNA in soybean event pDAB9582.816.15.1.

| SEQ ID NO: | Primer Name | Size (bp) | Sequence (5'to 3') | Purpose |
|---|---|---|---|---|
| SEQ ID NO: 4 | 81615_FW2 | 30 | TTACACCCTTAGGATC GAGACACTTAGAGC | confirmation of 5' border genomic DNA, used with AtUbi10RV1 or RV2; with 5'IREnd-01 or 5'IREnd-02 |
| SEQ ID NO: 5 | 81516_RV1 | 27 | GATTCATGTCCTTCCT AATGCGAATTG | confirmation of 3' border genomic DNA, used with 3'PATEnd05 or 3'PATEnd06 |
| SEQ ID NO: 6 | 81516_RV2 | 25 | AATTTCACATTTACCC CACTTGCGA | confirmation of 3' border genomic DNA, used with 3'PATEnd05 or 3'PATEnd06 |
| SEQ ID NO: 7 | 81516_RV3 | 28 | GGAGGTGCAGTGAGG AAGGTAATAATGA | confirmation of 3' border genomic DNA, used with 3'PATEnd05 or 3'PATEnd06DNA |

TABLE 3-continued

List of primers and their sequences used in the confirmation
of soybean genomic DNA in soybean event pDAB9582.816.15.1.

| SEQ ID NO: | Primer Name | Size (bp) | Sequence (5' to 3') | Purpose |
|---|---|---|---|---|
| SEQ ID NO: 8 | 5'IREnd-01 | 29 | CGAGCTTTCTAATTTC AAACTATTCGGGC | confirmation of 5' border genomic DNA, used with 81615_FW2 |
| SEQ ID NO: 9 | 5'IREnd-02 | 30 | TCCTAGATCATCAGTT CATACAAACCTCCA | confirmation of 5' border genomic DNA, used with 81615_FW2 |
| SEQ ID NO: 10 | AtUbi10RV1 | 29 | CGGTCCTAGATCATCA GTTCATACAAACC | confirmation of 5' border genomic DNA, used with 81615_FW2 |
| SEQ ID NO: 11 | AtUbi10RV2 | 28 | CACTCGTGTTCAGTCC AATGACCAATAA | confirmation of 5' border genomic DNA, used with 81615 FW1, FW2 or FW3 |
| SEQ ID NO: 12 | 3'PATEnd05 | 20 | GCTCCTCCAAGGCCA GTTAG | confirmation of 3' border genomic DNA, used with 81615_RV1, RV2 or RV3 |
| SEQ ID NO: 13 | 3'PATEnd06 | 20 | CCAGTTAGGCCAGTT ACCCA | confirmation of 3' border genomic DNA, used with 81615_RV1, RV2 or RV3 |

TABLE 4

Conditions for standard PCR amplification of the border regions and event-specific sequences in soybean event pDAB9582.816.15.1.

| Target Sequence | Primer Set | PCR Mixture | Pre-denature (° C./min) | Denature (° C./sec.) | Extension (° C./min:sec) | Final Extension (° C./min) |
|---|---|---|---|---|---|---|
| 5' border | 81615_FW2/ AtUbi10 RV1 | D | 95/3 | 98/10 | 68/4:00 32 cycles | 72/10 |
| 5' border | 81615_FW2/ 5'IREnd-01 | D | 95/3 | 98/10 | 68/4:00 32 cycles | 72/10 |
| 5' border | 81615_FW3/ 5'IREnd-01 | D | 95/3 | 98/10 | 68/4:00 32 cycles | 72/10 |
| 3' border | 3'PATEnd05/ 81615_RV1 | D | 95/3 | 98/10 | 68/4:00 32 cycles | 72/10 |
| 3' border | 3'PATEnd05/ 81615_RV2 | D | 95/3 | 98/10 | 68/4:00 35 cycles | 72/10 |
| 3'border | 3'PATEnd06/ 81615_RV1 | D | 95/3 | 98/10 | 68/4:00 32 cycles | 72/10 |
| 3'border | 3'PATEnd06/ 81615_RV2 | D | 95/3 | 98/10 | 68/4:00 32 cycles | 72/10 |
| Across the insert locus | 81615 FW2/ 81615_RV3 | D | 95/3 | 98/10 | 68/4:00 32 cycles | 72/10 |

TABLE 5

PCR mixture for standard PCR amplification of the border regions and event specific sequences in soybean event pDAB9582.816.15.1.

| Reagent | 1 x reaction (µL) |
|---|---|
| PCR Mixture A | |
| H20 | 0.8 |
| AccuPrime pfx SuperMix | 20 |
| 10 uM primer | 0.2 |
| gDNA digestion | 1 |

TABLE 5-continued

PCR mixture for standard PCR amplification of the border regions and event specific sequences in soybean event pDAB9582.816.15.1.

| Reagent | 1 x reaction (µL) |
|---|---|
| rxn vol: | 22 |
| PCR Mixture B | |
| H20 | 14.6 |
| 10X LA Taq buffer | 2 |
| MgCl2 (25 mM) | 0.6 |

TABLE 5-continued

PCR mixture for standard PCR amplification of the border regions and event specific sequences in soybean event pDAB9582.816.15.1.

| Reagent | 1 x reaction (µL) |
| --- | --- |
| dNTP (2.5 uM) | 1.6 |
| 10 uM primer | 0.1 |
| gDNA digestion | 1 |
| LA Taq (5 U/uL) | 0.1 |
| rxn vol: | 20 |
| PCR Mixture C | |
| H20 | 28 |
| 10X PCR buffer II (Mg-plus) | 5 |
| MgCl$_2$[25 mM] | 1.5 |
| dNTP[2.5 mM] | 8 |
| Adaptor PCR primer (10 µM) | 1 |
| GOI nested primer (10 µM) | 1 |
| DNA binded Beads | 5 |
| LA Taq (5 U/uL) | 0.5 |
| rxn vol: | 50 |
| PCR Mixture D | |
| H20 | 11.6 |
| 10X PCR buffer II (Mg-plus) | 2 |
| MgCl$_2$[25 mM] | 0.6 |
| dNTP[2.5 mM] | 3.2 |
| primer1 (10 µM) | 0.4 |
| primer2 (10 µM) | 0.4 |
| DNA Template | 0.2 |
| LA Taq (5 U/uL) | 1.6 |
| rxn vol: | 20 |

Example 3.1: Confirmation of Soybean Genomic Sequences

The 5' and 3' flanking borders aligned to a *Glycine max* whole genome shotgun sequence from chromosome 03, indicating that the transgene of soybean event pDAB9582.816.15.1 was inserted in soybean genome chromosome 03. To confirm the insertion site of soybean event pDAB9582.816.15.1 from the soybean genome, PCR was carried out with different pairs of primers (FIG. 2, Table 3, Table 4, and Table 5). Genomic DNA from soybean event pDAB9582.816.15.1 and other transgenic or non-transgenic soybean lines was used as a template. To confirm that the 5' border sequences are correct a primer designed to bind to the At Ubi10 promoter gene element, for example AtUbi10RV1, and a primer designed to bind to the cloned 5' end border on soybean genome chromosome 03, designated 81615_FW2, was used for amplifying the DNA segment that spans the At Ubi10 promoter gene element to 5' end border sequence. Similarly, for confirmation of the cloned 3' border sequence a pat specific primer, for example 3'PATEnd05, and primers designed according to the cloned 3' end border sequence, designated 81615_RV1 and 81615_RV2, were used for amplifying DNA segments that span the pat gene to 3' border sequence. DNA fragments with expected sizes were amplified only from the genomic DNA of soybean event pDAB9582.816.15.1 with each primer pair, but not from DNA samples from other transgenic soybean lines or the non-transgenic control. The results indicate that the cloned 5' and 3' border sequences are the flanking border sequences of the T-strand insert for soybean event pDAB95-82.816.15.1.

To further confirm the DNA insertion in the soybean genome, a PCR amplification spanning the soybean border sequences was completed on genomic DNA which did not contain the T-strand insert for soybean event pDAB9582.816.15.1. Primer 81615_FW2, designed according to the 5' end border sequence, and one primer 81615_RV3, designed for the 3' end border sequence, were used to amplify DNA segments which contained the locus where the pDAB9582 T-strand integrated. As expected, PCR reactions completed with the primer pair of 81615_FW2 and 81615_RV3 produced an approximately a 1.8 kb DNA fragment from all the other soybean control lines but not pDAB9582.816.15.1. Aligning the identified 5' and 3' border sequences of soybean event pDAB9582.816.15.1 with a *Glycine max* whole genome shotgun sequence from chromosome 03 revealed about 21 bp deletion from the original locus. (FIG. 3). These results demonstrated that the transgene of soybean event pDAB9582.816.15.1 was inserted into the site of soybean genome chromosome 03.

Example 4: Soybean Event pDAB9582.816.15.1 Characterization Via Southern Blot

Southern blot analysis was used to establish the integration pattern of soybean event pDAB9582.816.15.1. These experiments generated data which demonstrated the integration and integrity of the cry1Ac and cry1F transgenes within the soybean genome. Soybean event pDAB9582.816.15.1 was characterized as a full length, simple integration event containing a single copy of the cry1Ac and cry1F PTU from plasmid pDAB9582.

Southern blot data suggested that a T-strand fragment inserted into the genome of soybean event pDAB9582.816.15.1. Detailed Southern blot analysis was conducted using probes specific to the cry1Ac and cry1F gene, contained in the T-strand integration region of pDAB9582.816.15.1, and descriptive restriction enzymes that have cleavage sites located within the plasmid and produce hybridizing fragments internal to the plasmid or fragments that span the junction of the plasmid with soybean genomic DNA (border fragments). The molecular weights indicated from the Southern hybridization for the combination of the restriction enzyme and the probe were unique for the event, and established its identification patterns. These analyses also showed that the plasmid fragment had been inserted into soybean genomic DNA without rearrangements of the cry1Ac and cry1F PTU.

Example 4.1: Soybean Leaf Sample Collection and Genomic DNA (gDNA) Isolation

Genomic DNA was extracted from leaf tissue harvested from individual soybean plants containing soybean event pDAB9582.816.15.1. In addition, gDNA was isolated from a conventional soybean plant, Maverick, which contains the genetic background that is representative of the substance line, absent the cry1Ac and cry1F genes. Individual genomic DNA was extracted from lyophilized leaf tissue following the standard CTAB method. Following extraction, the DNA was quantified spectrofluorometrically using Pico Green reagent (Invitrogen, Carlsbad, Calif.).

Example 4.2: DNA Digestion and Separation

For Southern blot molecular characterization of soybean event pDAB9582.816.15.1, ten micrograms (10 µg) of genomic DNA was digested. Genomic DNA from the soybean event pDAB9582.816.15.1 and non-transgenic soybean line Maverick was digested by adding approximately five units of selected restriction enzyme per μg of DNA and the corresponding reaction buffer to each DNA sample. Each sample was incubated at approximately 37° C. overnight. The restriction enzymes AseI, HindIII, NsiI, and NdeI were used individually for the single digests (New England Biolabs, Ipswich, Mass.). The restriction enzymes NotI and ApaLI were used together for a double digestion (New England Biolabs, Ipswich, Mass.). In addition, a positive hybridization control sample was prepared by combining plasmid DNA, pDAB9582 with genomic DNA from the non-transgenic soybean variety, Maverick. The plasmid DNA/genomic DNA cocktail was digested using the same procedures and restriction enzyme as the test samples.

After the digestions were incubated overnight, 254 Quick-Precip Plus solution (Edge Biosystems, Gaithersburg, Md.) was added and the digested DNA samples were precipitated with isopropanol. The precipitated DNA pellet was resuspended in 15 μL of 1× loading buffer (0.01% bromophenol blue, 10.0 mM EDTA, 10.0% glycerol, 1.0 mM Tris pH 7.5). The DNA samples and molecular size markers were then electrophoresed through 0.85% agarose gels with 0.4×TAE buffer (Fisher Scientific, Pittsburgh, Pa.) at 35 volts for approximately 18-22 hours to achieve fragment separation. The gels were stained with ethidium bromide (Invitrogen, Carlsbad, Calif.) and the DNA was visualized under ultraviolet (UV) light.

Example 4.3: Southern Transfer and Membrane Treatment

Southern blot analysis was performed essentially as described by Memelink, et al. (1994). Briefly, following electrophoretic separation and visualization of the DNA fragments, the gels were depurinated with 0.25M HCl for approximately 20 minutes, and then exposed to a denaturing solution (0.4 M NaOH, 1.5 M NaCl) for approximately 30 minutes followed by neutralizing solution (1.5 M NaCl, 0.5 M Tris pH 7.5) for at least 30 minutes. Southern transfer was performed overnight onto nylon membranes using a wicking system with 10×SSC. After transfer, the DNA was bound to the membrane by UV crosslinking followed by briefly washing membrane with a 2×SSC solution. This process produced Southern blot membranes ready for hybridization.

Example 4.4: DNA Probe Labeling and Hybridization

The DNA fragments bound to the nylon membrane were detected using a labeled probe (Table 6). Probes were generated by a PCR-based incorporation of a digoxigenin (DIG) labeled nucleotide, [DIG-11]-dUTP, into the DNA fragment amplified from plasmid pDAB9582 using primers specific to gene elements. Generation of DNA probes by PCR synthesis was carried out using a PCR DIG Probe Synthesis Kit (Roche Diagnostics, Indianapolis, Ind.) following the manufacturer's recommended procedures.

Labeled probes were analyzed by agarose gel electrophoresis to determine their quality and quantity. A desired amount of labeled probe was then used for hybridization to the target DNA on the nylon membranes for detection of the specific fragments using the procedures essentially as described for DIG Easy Hyb Solution (Roche Diagnostics, Indianapolis, Ind.). Briefly, nylon membrane blots containing fixed DNA were briefly washed with 2×SSC and pre-hybridized with 20-25 mL of pre-warmed DIG Easy Hyb solution in hybridization bottles at approximately 45-55° C. for about 2 hours in a hybridization oven. The pre-hybridization solution was then decanted and replaced with ~15 mL of pre-warmed DIG Easy Hyb solution containing a desired amount of specific probes denatured by heating in a thermal cycler for approximately five minutes. The hybridization step was then conducted at approximately 45-55° C. overnight in the hybridization oven.

At the end of the probe hybridization, DIG Easy Hyb solutions containing the probes were decanted into clean tubes and stored at approximately −20° C. These probes could be reused for twice according to the manufacturer's recommended procedure. The membrane blots were rinsed briefly and washed twice in clean plastic containers with low stringency wash buffer (2×SSC, 0.1% SDS) for approximately five minutes at room temperature, followed by washing twice with high stringency wash buffer (0.1×SSC, 0.1% SDS) for 15 minutes each at approximately 65° C. The membrane blots briefly washed with 1× Maleic acid buffer from the DIG Wash and Block Buffer Set (Roche Diagnostics, Indianapolis, Ind.) for approximately 5 minutes. This was followed by blocking in a 1× blocking buffer for 2 hours and an incubation with anti-DIG-AP (alkaline phosphatase) antibody (Roche Diagnostics, Indianapolis, Ind.) in 1× blocking buffer also for a minimum of 30 minutes. After 2-3 washes with 1× washing buffer, specific DNA probes remain bound to the membrane blots and DIG-labeled DNA standards were visualized using CDP-Star Chemiluminescent Nucleic Acid Detection System (Roche Diagnostics, Indianapolis, Ind.) following the manufacturer's recommendation. Blots were exposed to chemiluminescent film for one or more time points to detect hybridizing fragments and to visualize molecular size standards. Films were developed with an All-Pro 100 Plus film developer (Konica Minolta, Osaka, Japan) and images were scanned. The number and sizes of detected bands were documented for each probe. DIG-labeled DNA Molecular Weight Marker II (DIG MWM II) and DIG-labeled DNA Molecular Weight Marker VII (DIG MWM VII), visible after DIG detection as described, were used to determine hybridizing fragment size on the Southern blots.

TABLE 6

Location and length of probes used in Southern analysis.

| Probe Name | Genetic Element | Length (bp) |
| --- | --- | --- |
| Cry1Ac | cry1Ac | 1720 |
| Cry1F | cry1F | 1746 |
| specR | Spectinomycin resistance gene | 750 |
| OriRep | Ori Rep | 852 |
| trfA | Replication initiation protein trfA | 1119 |

Example 4.5: Southern Blot Results

Expected and observed fragment sizes with a particular digest and probe, based on the known restriction enzyme sites of the cry1Ac and cry1F PTU, are given in Table 7. Two types of fragments were identified from these digests and hybridizations: internal fragments where known enzyme sites flank the probe region and are completely contained within the insertion region of the cry1Ac and cry1F PTU, and border fragments where a known enzyme site is located at one end of the probe region and a second site is expected in the soybean genome. Border fragment sizes vary by event because, in most cases, DNA fragment integration sites are unique for each event. The border fragments provide a means to locate a restriction enzyme site relative to the integrated DNA and to evaluate the number of DNA insertions. Southern blot analyses completed on multiple generations of soybean containing soybean event pDAB9582.816.15.1 produced data which suggested that a low copy, intact cry1Ac and cry1F PTU from plasmid pDAB9582 was inserted into the soybean genome of soybean event pDAB9582.816.15.1.

Table 7. Predicted and observed hybridizing fragments in Southern blot analysis. 1. Expected fragment sizes are based on the plasmid map of pDAB9582. 2. Observed fragment sizes are considered approximately from these analyses and are based on the indicated sizes of the DIG-labeled DNA Molecular Weight Marker II and Mark VII fragments.

| DNA Probe | Restriction Enzymes | Samples | Expected Fragment Sizes (bp)[1] | Observed Fragment Size (bp)[2] |
|---|---|---|---|---|
| Cry1Ac | AseI | pDAB9582 | 13476 | >14000 |
| | | Maverick | none | none |
| | | Soybean Event pDAB9582.816.15.1 | >7286 | ~8500 |
| | Nsi I | pDAB9582 | 15326 | >15000 |
| | | Maverick | none | none |
| | | Soybean Event pDAB9582.816.15.1 | >9479 | >10000 |
| | Not I + ApaLI | pDAB9582 | 4550 | ~4500 |
| | | Maverick | none | none |
| | | Soybean Event pDAB9582.816.15.1 | 4550 | ~4500 |
| Cry1F | NdeI | pDAB9582 | 8071 | ~8000 |
| | | Maverick | none | none |
| | | Soybean Event pDAB9582.816.15.1 | >5569 | ~7500 |
| | Nsi I | pDAB9582 | 11044 | 11000 |
| | | Maverick | none | none |
| | | Soybean Event pDAB9582.816.15.1 | >9479 | >10000 |
| | Hind III | pDAB9582 | 7732 | ~7700 |
| | | Maverick | none | none |
| | | Soybean Event pDAB9582.816.15.1 | 7732 | ~7700 |
| SpecR | NsiI | pDAB9582 | 15320 | ~15000 |
| | | Maverick | none | none |
| | | Soybean Event pDAB9582.816.15.1 | none | none |
| trfA | NsiI | pDAB9582 | 15320 | ~15000 |
| | | Maverick | none | none |
| | | Soybean Event pDAB9582.816.15.1 | none | none |
| oriREP | NdeI | pDAB9582 | 5239 | ~5000 |
| | | Maverick | none | none |
| | | Soybean Event pDAB9582.816.15.1 | none | none |

The restriction enzymes AseI and NsiI bind and cleave unique restriction sites in plasmid pDAB9582. Subsequently, these enzymes were selected to characterize the cry1Ac gene insert in soybean event pDAB9582.816.15.1 border fragments of >7286 bp or >9479 bp were predicted to hybridize with the probe following AseI and NsiI digests, respectively (Table 7). Single cry1Ac hybridization bands of about 8500 and >10000 bp were observed when AseI and NsiI digests were used, respectively. The hybridization of the probe to bands of this size suggests the presence of a single site of insertion for the cry1Ac gene in the soybean genome of soybean event pDAB9582.816.15.1. Restriction enzymes NotI and ApaLI were selected to perform a double digestion and to release a fragment which contains the cry1Ac plant transcription unit (PTU; promoter/gene/terminator) (Table 7). The predicted 4550 bp fragments were observed with the probe following NotI and ApaLI double digestion. Results obtained with the enzyme digestion of the pDAB9582.816.15.1 samples followed by probe hybridization indicated that an intact cry1Ac PTU from plasmid pDAB9582 was inserted into the soybean genome of soybean event pDAB9582.816.15.1.

The restriction enzymes NdeI and NsiI bind and cleave restriction sites in plasmid pDAB9582. Subsequently, these enzymes were selected to characterize the cry1F gene insert in soybean event pDAB9582.816.15.1. Border fragments of >5569 bp and >9479 were predicted to hybridize with the probe following the NdeI and NsiI digests, respectively (Table 7). Single cry1F hybridization bands of ~7500 bp and >10000 bp were observed when NdeI and NsiI were used, respectively. The hybridization of the probe to bands of this size suggests the presence of a single site of insertion for the cry1F gene in the soybean genome of soybean event pDAB9582.816.15.1. Restriction enzyme, HindIII, was selected to release a fragment which contains the cry1F plant transcription unit (PTU; promoter/gene/terminator) (Table 7). The predicted 7732 bp fragment was observed with the probe following the HindIII digestions. Results obtained with the enzyme digestion of the pDAB9582.816.15.1 samples followed by probe hybridization indicated that an intact cry1F PTU from plasmid pDAB9582 was inserted into the soybean genome of soybean event pDAB9582.816.15.1.

Example 4.6: Absence of Backbone Sequences

Southern blot analysis was also conducted to verify the absence of the spectinomycin resistance gene (specR), On Rep element and replication initiation protein trfA (trf A element) in soybean event pDAB9582.816.15.1. No specific hybridization to spectinomycin resistance, On Rep element or trf A element is expected when appropriate positive (pDAB9582 added to Maverick genomic DNA) and negative (Maverick genomic DNA) controls are included for Southern analysis. Following the NsiI digestion and hybridization with the specR specific probe, one expected size band of 15320 bp was observed in the positive control sample (pDAB9582 added to Maverick genomic DNA). The specR probe did not hybridize to samples of the negative control and soybean event pDAB9582.816.15.1. Similarly, one expected size band of 15320 bp was detected in the positive control sample (pDAB9582 plus maverick) but absent from the samples of the negative control and soybean event pDAB9582.816.15.1 after NsiI digestion and hybridization with trfA probe. Another expected size band of 5329 bp was detected in the positive control sample (pDAB9582 added to Maverick genomic DNA) but absent from the samples of the negative control and soybean event pDAB9582.816.15.1 after NdeI digestion and hybridization with OriRep specific probe. These data indicate the absence of spectinomycin resistance gene, On Rep element and replication initiation protein trfA in soybean event pDAB9582.816.15.1.

Example 5: Agronomic and Yield Field Trial and Herbicide Tolerance

Replicated agronomic trials were run to compare the agronomic efficacy of soybean event pDAB9582.816.15.1 with the null isoline—Maverick. The majority of the field trials were planted at distinct geographical locations throughout the United States where the soybean variety which contains soybean event pDAB9582.816.15.1 is cultivated. Additional field trials were completed outside of these locations, and were selected to expose the soybean variety which contains soybean event pDAB9582.816.15.1 to potential stresses that occur from growing in non-preferred locations. Due to environmental variability within a small number of the field trials, some of the sites were discontinued from the study.

The experiment was set up as a randomized complete block design with two replications per location. There were eight entries including soybean event pDAB9582.816.15.1. Each plot consisted of two rows, 12.5 feet long, planted 30 inches apart. Throughout the season, field plots were maintained under normal agronomic practices and kept free from weeds.

Seed for the study was produced in winter nursery in Puerto Rico during the, Seed of soybean event pDAB9582.816.15.1 and Maverick were grown in the same nursery and treated in a similar manner in order to minimize any seed source variability. Next, the seed was shipped back to North America where it was packaged and distributed to the various planting locations. Throughout the season a number of agronomic characteristics were measured. These characteristics and the growth stage when the data were collected are listed in Table 8.

TABLE 8

List of agronomic characteristics measured in field trials to compare soybean event pDAB9582.816.15.1 with Maverick.

| Characteristic Measured | Growth stage when measurement taken |
| --- | --- |
| 1. Emergence: Stand count divided by the number of seeds planted in a one meter section multiplied by 100. | Calculated based on early stand count |
| 2. Seedling vigor: Percent vigor with 0% representing a plot with all dead plants and 100% representing plots that look very healthy. | V1-V3 |
| 3. Days to Flowering: Days from planting when 50% of the plants in the plot began to flower. | R1 |
| 4. Stand count at R2: Number of plants in a representative one meter section of row at the R2 growth stage. | R2 |
| 5. Disease incidence: Severity of disease in the plot rated on a scale of 0-100%. | R6 |
| 6. Insect damage: Percentage of plant tissue in the plot damaged by insects. | R6 |
| 7. Plant height: Average height in centimeters of the plants in each plot measured from the soil surface to the tip after leaves have fallen. | R8 |
| 8. Lodging: Percent lodging at harvest time with 0% = no lodging and 100% = all plants in a plot flat on the ground. | R8 |
| 9. Days to maturity. Days from planting when 95% of the pods in a plot reached their dry down color. | R8 |
| 10. Shattering: Percentage of pods shattered per plot. | R8 |
| 11. Yield: Bushels per acre adjusting to 13% moisture. | R8 |
| 12. 100 seed weight: For each plot count out 100 seeds and record the weight in grams. | R8 |

At the end of the growing season, data from all locations were combined and an across location analysis was performed. Data analysis was carried out using JMP® Pro 9.0.3 (SAS, Cary, N.C.). A mixed model was used for analysis where entry was considered a fixed effect and location, location by entry, and replication effects were considered random. Least square means from the analysis are reported in Table 9. For variables where a significant entry effect was measured a subsequent mean separation was performed using Student's T test to make the comparison between Maverick and soybean event pDAB9582.816.15.1. The probability level for determining significance was set at p=0.05.

TABLE 9

Least square means from the across location analysis comparing soybean event pDAB9582.816.15.1 to Maverick. Levels not connected by the same letter are significantly different at p = 0.05 according to Student's T test.

| Name | Soybean Event pDAB9582.816.15.1 | Maverick |
| --- | --- | --- |
| Emergence (%) | 84 (A) | 89 (A) |
| Vigor (V1-V3) | 85 (A) | 90 (A) |
| Days to Flowering (days from planting) | 44.9 (A) | 43.0 (B) |
| Stand Count at R2 (plants/m) | 24 (A) | 25 (A) |
| Disease Incidence at R6 (%) | 2 (A) | 2 (A) |
| Insect Damage R6 (%) | 6 (A) | 7 (A) |
| Height (cm) | 110 (A) | 114 (A) |
| Maturity (days from planting) | 123 (A) | 122 (B) |
| Lodging (%) | 24 (A) | 21 (A) |
| Shattering (%) | 0 (A) | 0 (A) |
| Yield (bu/acre) | 47.6 (A) | 50.5 (A) |
| 100 Seed Weight (g) | 12.3 (B) | 13.2 (A) |

All traits measured with the exception of days to flowering, maturity and 100 seed weight exhibited parity between soybean event pDAB9582.816.15.1 and Maverick. Soybean event pDAB.816.15.1 flowered about 2 days later than Maverick. The two day delay is not a severe delay for producers, and does not impair crop performance. Plots were considered to be flowering when approximately 50% of the plants in a plot exhibited open flowers. Soybean event pDAB9582.816.15 also matured one day later than Maverick at the end of the season, but this delay did not result in a meaningful agronomic difference which would impair crop performance. Likewise, 100 seed weight of soybean event pDAB9582.816.15 was statistically different than Maverick, but this did not result in a significant reduction in yield. The results indicate that soybean event pDAB9582.816.15 may develop differently than Maverick but the difference is minimal and not outside the normal range of commercially grown soybeans.

To test the herbicide tolerance of soybean event pDAB9582.816.15.1 the event was planted in an efficacy trial Santa Isabel, Puerto Rico. The cultivar Maverick, which was originally transformed to produce soybean event pDAB9582.816.15.1, was planted in each nursery and included as a control in the experiments. Seed for the $T_3$ nursery was derived from single plant selections at the $T_2$ stage and seed for the $T_4$ nursery was derived from single plant selections at the $T_3$ stage. Four lineages of the event were tested at each generation. Each lineage was planted in a plot which was 4 rows wide and 7.5 feet long. The spacing between rows was 30 inches. Plots were grown under lights for approximately 2.5 weeks to compensate for the short day length in Puerto Rico. Each nursery was sprayed with glufosinate at a rate of 411 g ae/ha. One plot of the control plants, Maverick, was sprayed with the same rate of glufosinate and a second plot was non-sprayed and used as control comparison for the event. Soybean event pDAB9582.816.15.1 showed tolerance to the glufosinate herbicide application. In contrast, none of the Maverick plants were tolerant to the herbicide treatments.

Example 6: Characterization of Insecticidal Activity for Soybean Event pDAB 9582.816.15.1

Field and greenhouse evaluations were conducted to characterize the level of plant protection provided by the Cry1Ac and Cry1F proteins in soybean event pDAB9582.816.15.1 against soybean pests including the following Lepidopteran insects, including *Anticarsia gemmatalis* (velvetbean caterpillar), *Pseudoplusia includens* (soybean looper), *Spodoptera frugiperda* (fall armyworm) and *Heliothis virescens* (tobacco budworm).

A greenhouse trial was conducted on approximately four week old plants. Fifteen plants were used to evaluate soybean event pDAB9582.816.15.1 and the Maverick control. For each insect species tested (*A. gemmatalis, P. includes, and S. frugiperda* neonate larvae), three leaf discs were cut from each plant for a total of 45 leaf discs per plant per insect species. The 1.4 cm leaf punches were placed in a test arena on top of 2% water agar, infested with one neonate larvae and sealed with a perforated plastic lid.

Mortality and leaf consumption were rated after infestation. Larvae that were not responsive to gentle probing were considered dead. The mortality rates of the insects which were placed on plant materials containing soybean event pDAB9582.816.15.1 were significantly higher (86% mortality for *Spodoptera frugiperda*, 100% mortality for *Anticarsia gemmatalis*, and 100% mortality for *Pseudoplusia includens*) than the insects which which were placed on the Maverick controls. Table 10. Leaf damage was assessed by visually scoring the percentage of leaf disc consumed by the insect. The results obtained from the greenhouse experiments indicated that soybean event pDAB9582.816.15.1 sustained significantly lower leaf damage and higher insect mortality as compared to Maverick control plants for infestation from *Anticarsia gemmatalis, Pseudoplusia includens*, and *Spodoptera frugiperda*.

An efficacy evaluation of field-grown soybean event pDAB9582.816.15.1 plants was conducted by collecting leaf samples from seed increase nursery plots in Santa Isabel, Puerto Rico and sending these leaves to Indianapolis, Ind. for bioassay. The nursery plot for the $T_3$ soybean event pDAB9582.816.15.1 plants consisted of approximately 180 plants arranged in four rows. Each row was 2.3 m long and spaced 76.2 cm apart; individual plants were spaced 5.1 cm apart within each row. The bioassays were performed on one fully-expanded, mainstem trifoliate leaf, located approximately four nodes below the meristem. The trifoliate leaf tissue was excised from 10 individual soybean plants bearing event pDAB9582.816.15.1 and 10 individual Maverick plants. The leaves were packed and transferred to the laboratory. In the laboratory, one or two 3.33 cm diameter leaf discs were punched from each trifoliate leaf to provide a total of 16 leaf discs. Each leaf disc was placed in a test arena on top of 2% agar, infested with one neonate *S. frugiperda* larva, and sealed with a perforated plastic lid. The leaf discs were held in a controlled environment chamber for 7 days, at which time mortality and leaf consumption were rated. Larvae not responsive to gentle probing were considered dead. Leaf damage was assessed by visually scoring the percentage of leaf punch consumed by the insect.

Mortality and leaf consumption were rated after infestation. Larvae that were not responsive to gentle probing were considered dead. The mortality rates of the insects which were placed on plant materials containing soybean event pDAB9582.816.15.1 were significantly higher (68% mortality for *Spodoptera frugiperda*) than the insects which which were placed on the Maverick controls (0% mortality for *Spodoptera frugiperda*). Table 10. Leaf damage was assessed by visually scoring the percentage of leaf disc consumed by the insect. The results obtained from this leaf bioassay indicated *Spodoptera frugiperda* larvae exposed to soybean event pDAB9582.816.15.1 sustained significantly lower leaf damage and insect survival (also described as higher insect mortality) than *Spodoptera frugiperda* larvae exposed to the Maverick control plants.

The efficacy of soybean event pDAB9582.816.15.1 was evaluated in a first field trial (First Field Trial in Table 10). Soybean seeds from the $T_4$ generation, containing soybean event pDAB9582.816.15.1 and seeds of the untransformed soybean variety Maverick were planted in a randomized complete block design with 2 replicates. Each replicate plot consisted of 2 rows, 2.3 m in length and spaced 0.76 m apart. There were 40 seeds planted per row, spaced 5.7 cm apart within the row. The trial was planted and one replicate was sprayed with glufosinate herbicide at 411 g ae/ha and the other replicate was not, resulting in only the unsprayed replicate of Maverick plants surviving for bioassay.

Leaves for the bioassay were collected when the soybean plants were in the R2 growth stage. Several days before leaves were collected for bioassay, leaf punches were taken from the leaf one node lower (and an older leaf) on the same plants and analyzed for expression of Cry1Ac and Cry1F proteins using an ELISA method similar to that described in Example 2 (Table 12). Fully-expanded, mainstem trifoliate leaves, showing no signs of damage or discoloration and located four nodes below the meristem, were excised for bioassay. A single trifoliate leaf was excised from each of 15 plants per replicate. The leaves were stored at 15° C. and bioassayed. The leaflets of each trifoliate were excised and a single 3.33 cm diameter disc cut from the center of each soybean event pDAB9582.816.15.1 leaflet and two 3.33 cm diameter leaf discs were cut from each Maverick leaflet. These leaf discs were placed individually in separate, labeled wells of 32-well plastic bioassay trays; each well containing a thin layer of agar. A single, neonate *P. includens* larva, neonate *A. gemmatalis* larva, or neonate *S. frugiperda* larva was placed on each leaf disc. The bioassay trays were sealed with adhesive plastic sheets perforated to provide ventilation. For each species, 30 larvae were exposed to leaf tissue from soybean event pDAB9582.816.15.1, and 30 larvae were exposed to leaf tissue from Maverick. The plastic trays holding the infested leaf discs were held at 25° C. and 40% relative humidity (RH). After 7 days, larvae were determined to be dead (no movement when stimulated with a sharp probe), stunted (smaller in size than larvae held on Maverick leaves), or alive (normal in size and response to stimulus).

Mortality was rated after infestation. The mortality rates of the insects which were placed on plant materials containing soybean event pDAB9582.816.15.1 were significantly higher (97% mortality for *Spodoptera frugiperda*, 100% mortality for *Anticarsia gemmatalis*, and 100% mortality for *Pseudoplusia includens*) than the insects which which were placed on the Maverick controls. Table 10. The results obtained from this leaf bioassay indicated *Spodoptera frugiperda, Anticarsia gemmatalis*, and *Pseudoplusia includens* larvae exposed to soybean event pDAB9582.816.15.1 sustained significantly lower insect survival (also described as higher insect mortality) than *Spodoptera frugiperda, Anticarsia gemmatalis*, and *Pseudoplusia includens* larvae exposed to the Maverick control plants.

The efficacy of soybean event pDAB9582.816.15.1 was evaluated in a second seperate field trial (Second Field Trial in Table 10). Soybean seeds from the $T_4$ generation, containing soybean event pDAB9582.816.15.1 and seeds of the untransformed soybean variety Maverick were planted in a randomized complete block design with 4 replicates. Each replicate plot consisted of 4 rows, 6.1 m in length and spaced 1.02 m apart. There were 160 seeds planted per row, spaced 3.8 cm apart within the row. Additional rows of Maverick were planted between and around the trial plots to attract native insect pest populations.

Leaves for the bioassay were collected when the soybean plants were in the R2 growth stage. Leaves for an additional bioassay were collected from the same plants when the soybean plants were in the R5 growth stage. Several days before leaves were collected for each bioassay, leaf punches were taken from the leaf one node lower on the same plants and analyzed for Cry 1Ac and Cry 1F proteins using an ELISA method similar to that described in Example 2 (Table 12). Fully-expanded, mainstem trifoliate leaves, showing no signs of damage or discoloration and located four nodes below the meristem, were excised for bioassay. A single trifoliate leaf was excised from each of 15 plants per replicate; 4 trifoliates per replicate were used for the bioassay of *P. includens,* 4 trifoliates per replicate were used for the bioassay of *S. frugiperda,* 4 trifoliates per replicate were used for the bioassay of *H. virescens,* and 3 trifoliates per replicate were used for the bioassay of *A. gemmatalis.* The two side leaflets of each trifoliate were excised and placed in separate, labeled petri plates containing a thin layer of agar. Two second instar larvae of *P. includens, A. gemmatalis, S. frugiperda,* or *H. virescens* were placed on each leaflet. For *P. includens, S. frugiperda,* and *H. virescens,* 64 larvae were exposed to leaf tissue from soybean event pDAB9582.816.15.1 and Maverick plants. For *A. gemmatalis,* 48 larvae were exposed to leaf tissue from soybean event pDAB9582.816.15.1 and Maverick control plants. The petri plates holding the infested leaflets were covered with lids and held at 25° C. and 40% RH. After 4 days, larvae were determined to be dead (no movement when stimulated with a sharp probe), moribund (larva responds to stimulus but unable to right itself if placed on side), stunted (smaller in size than larvae held on Maverick leaves), or alive (normal in size and response to stimulus).

The bioassay procedure at R5 stage was the same as the procedure used at R2 stage with the exception that for *S. frugiperda* and *H. virescens,* all three leaflets were excised from each trifoliate and a single, second instar larva was placed on each leaflet. This resulted in 48 larvae of *S. frugiperda* and *H. virescens* being exposed to leaflets from soybean event pDAB9582.816.15.1 and Maverick.

Mortality was rated after infestation for both the R2 and R5 leaf bioassays. The mortality rates of the insects which were placed on plant materials containing soybean event pDAB9582.816.15.1 were significantly higher (69% mortality for the R2 leaf bioassay and 54% mortality for the R5 leaf bioassay of *Spodoptera frugiperda,* 100% mortality for both the R2 and R5 leaf bioassays of *Anticarsia gemmatalis,* 95% mortality for the R2 leaf bioassay and 70% mortality for the R5 leaf bioassay of *Heliothis virescens,* and 100% mortality for the R2 leaf bioassay and 98% mortality for the R5 leaf bioassay of *Pseudoplusia includens*) than the insects which which were placed on the Maverick controls. Table 10. The results obtained from this leaf bioassay indicated *Spodoptera frugiperda, Anticarsia gemmatalis, Pseudoplusia includens* and *Heliothis virescens* larvae exposed to soybean event pDAB9582.816.15.1 sustained significantly lower insect survival (also described as higher insect mortality) than *Spodoptera frugiperda, Anticarsia gemmatalis, Pseudoplusia includens* and *Heliothis virescens* larvae exposed to the Maverick control plants.

Soybean pods were collected from soybean event pDAB9582.816.15.1 and Maverick soybean plants grown at the second field trial, and bioassayed with *H. virescens* larvae. The two uppermost pods on the mainstem were excised from six plants selected at random within each replicate plot. Each set of pods was placed in a plastic petri dish and infested by a single second instar *H. virescens* larva. The experiment was designed so that 24 larvae would be exposed to a set of pods from that had been harvested from soybean event pDAB9582.816.15.1 and Maverick control plants. The petri dishes were held under the same conditions as the excised leaf bioassay described previously. After 2 days, survival of the *H. virescens* larvae was observed using the procedure described for the leaf bioassays.

Mortality was rated after infestation of the soybean pods. The mortality rates of the insects which were placed on soybean pods containing soybean event pDAB9582.816.15.1 were significantly higher (50% mortality for the soybean pod bioassay of *Heliothis virescens*) than the insects which which were placed on the Maverick control pods. Table 10. The results obtained from this assay on field-grown soybean pods indicated that *Heliothis virescens* larvae exposed to soybean event pDAB9582.816.15.1 sustained significantly lower insect survival (also described as higher insect mortality) than *Heliothis virescens* larvae exposed to the Maverick control plants.

The terminals (the uppermost section of mainstem bearing two to three expanding trifoliate leaves and a cluster of immature pods) of soybean event pDAB9582.816.15.1 and Maverick control soybean plants were infested in the field with *H. virescens* eggs. Sections of cheese cloth bearing approximately twenty eggs from *H. virescens* were placed on the terminals of five plants selected at random within each replicate plot (20 plants tested in total), and held in place with a plastic-covered paper clip. Cloth mesh bags were placed over the terminals and the open end of the mesh bag was secured around the mainstem with a twist-tie. Egg hatching was monitored daily in a representative set of mesh bags. After all the eggs had hatched, the number of live *H. virescens* larvae in each mesh bag attached to the five plants was counted.

The average number of live insect larvae which were placed on soybean terminals of soybean event pDAB9582.816.15.1 was significantly lower (0.00 number of insects for the soybean terminal bioassay of *Heliothis virescens*) than the insects which were placed on the terminals of the Maverick controls. Table 11. The results obtained from this assay indicated that *Heliothis virescens* larvae exposed to soybean event pDAB9582.816.15.1 sustained significantly lower numbers of insect survival than *Heliothis virescens* larvae exposed to the Maverick control plants.

Counts of native *P. includens* larvae in the trial plots were made once a week over a four week period. The center two rows of each plot were sampled. A 91 cm×91 cm white cloth was placed at a randomly selected location between the center two rows. The plants in the section of row adjacent to one edge of the sheet were bent over the cloth and shaken 15 times to dislodge any insects present. This process was repeated for the row on the opposite edge of the cloth.

was significantly lower than *Pseudoplusia includens* infestation exposed to the Maverick control plants.

The results obtained from these replicated experiments indicated that Lepidoptera larvae exposed to soybean event pDAB9582.816.15.1 sustained significantly lower survival than larvae exposed to the Maverick control plants for all insect species tested. Thus, the soybean event pDAB9582.816.15.1 has insecticidal activity over this broad range of pest insects.

TABLE 10

Insect mortality counts for Lepidopteran insects which were bioassayed on soybean leaf and pod material from soybean event pDAB9582.816.15.1 as compared to control Maverick plants.

| Trial | Pest species and stage tested | Test | Soybean event pDAB9582.816.15.1 | | Maverick | |
|---|---|---|---|---|---|---|
| | | | Number of dead larvae | Total larvae tested | Number of dead larvae | Total larvae tested |
| Greenhouse | *A. gemmatalis* neonate larvae | leaf bioassay | 45 | 45 | 3 | 45 |
| Greenhouse | *P. includens* neonate larvae | leaf bioassay | 45 | 45 | 3 | 45 |
| Greenhouse | *S. frugiperda* neonate larvae | leaf bioassay | 39 | 45 | 0 | 45 |
| Santa Isabel, PR | *S. frugiperda* neonate larvae | leaf bioassay | 11 | 16 | 0 | 16 |
| First Field Trial | *A. gemmatalis* neonate larvae | leaf bioassay | 30 | 30 | 3 | 30 |
| | *P. includens* neonate larvae | leaf bioassay | 30 | 30 | 6 | 30 |
| | *S. frugiperda* neonate larvae | leaf bioassay | 29 | 30 | 2 | 30 |
| Second Field Trial | *A. gemmatalis* $2^{nd}$ instar larvae | R2 leaf bioassay | 48 | 48 | 0 | 48 |
| | *P. includens* $2^{nd}$ instar larvae | R2 leaf bioassay | 64 | 64 | 0 | 64 |
| | *S. frugiperda* $2^{nd}$ instar larvae | R2 leaf bioassay | 44 | 64 | 0 | 64 |
| | *H. virescens* $2^{nd}$ instar larvae | R2 leaf bioassay | 61 | 64 | 0 | 64 |
| | *A. gemmatalis* $2^{nd}$ instar larvae | R5 leaf bioassay | 48 | 48 | 4 | 48 |
| | *P. includens* $2^{nd}$ instar larvae | R5 leaf bioassay | 63 | 64 | 0 | 64 |
| | *S. frugiperda* $2^{nd}$ instar larvae | R5 leaf bioassay | 26 | 48 | 1 | 48 |
| | *H. virescens* $2^{nd}$ instar larvae | R5 leaf bioassay | 34 | 48 | 3 | 48 |
| | *H. virescens* $2^{nd}$ instar larvae | pod bioassay | 12 | 24 | 4 | 24 |

Larvae were counted by species and size: larvae <6 mm in length were counted as small larvae and larvae >6 mm in length were counted as large larvae. All insects were removed from the cloth before taking the next measurement. The cloth was moved to a second randomly selected location between the two center rows and the sampling process was repeated, resulting in two subsamples per plot at each sampling date.

The average number of insects which were counted over a 1.82 m row of soybean event pDAB9582.816.15.1 was significantly lower (0.00 number of insects for *Pseudoplusia includens*) than the number of insects which were counted over a 1.82 m row of the Maverick controls. Table 11. The results obtained from this assay indicated that *Pseudoplusia includens* infestation of soybean event pDAB9582.816.15.1

TABLE 11

Average number of live Lepidopteran insects which were present on soybean event pDAB9582.816.15.1 as compared to control Maverick plants.

| Location | Pest species and stage counted | Test | Average number of live larvae | |
|---|---|---|---|---|
| | | | Soybean Event pDAB9582.816.15.1 | Maverick |
| Second Field Trial | *H. virescens* larvae | terminal bioassay | 0.00 per terminal | 3.75 per terminal |
| | *P. includens* small + large larvae | First week field count | 0.00 per 1.82 m of row | 2.25 per 1.82 m of row |
| | *P. includens* small + large larvae | Second week field count | 0.50 per 1.82 m of row | 6.25 per 1.82 m of row |

TABLE 11-continued

Average number of live Lepidopteran insects which were present on soybean event pDAB9582.816.15.1 as compared to control Maverick plants.

| Location | Pest species and stage counted | Test | Average number of live larvae | |
|---|---|---|---|---|
| | | | Soybean Event pDAB9582.816.15.1 | Maverick |
| | P. includens small + large larvae | Third week field count | 0.00 per 1.82 m of row | 22.75 per 1.82 m of row |
| | P. includens small + large larvae | Fourth week field count | 0.00 per 1.82 m of row | 4.00 per 1.82 m of row |

TABLE 12

Mean expression level of different transgenic proteins isolated from soybean event pDAB9582.816.15.1 plant materials which were used for insect bioassays.

| | | | ng/cm² of protein isolated from leaf tissue | | | |
|---|---|---|---|---|---|---|
| | | | Soybean Event pDAB9582.816.15.1 | | Maverick | |
| Field Trial | Plant stage tested | Tissue tested | Cry 1Ac | Cry 1F | Cry 1Ac | Cry 1F |
| First Field Trial | R2 | leaf | 6.8 | 52.9 | 0.0 | 0.0 |
| Second Field Trial | R2 | leaf | 0.79 | 2.73 | 0.0 | 0.0 |
| Second Field Trial | R5 | leaf | 0.39 | 2.28 | 0.0 | 0.0 |

Example 7: Expected Sequence of Soybean Event pDAB9582.816.15.1

SEQ ID NO:14 provides the expected sequence of soybean event pDAB9582.816.15.1. This sequence contains the 5' genomic flanking sequence, the expected T-strand insert of pDAB9582 and 3' genomic flanking sequences. With respect to SEQ ID NO:14, residues 1-1273 are 5' genomic flanking sequence, residues 1274-13658 are residues of the pDAB9582 T-strand insert, 13659-13821 are residues of a rearrangement from the pDAB9582 plasmid and residues 13822-15170 are 3' flanking sequence. The junction sequence or transition with respect to the 5' end of the insert thus occurs at residues 1273-1274 of SEQ ID NO:14. The junction sequence or transition with respect to the 3' end of the insert thus occurs at residues 13658-13659 of SEQ ID NO:14.

It should be noted that SEQ ID NO:14 is the expected representation of soybean event pDAB9582.816.15.1 and was assembled from an alignment of SEQ ID NO:1, SEQ ID NO:2, and the t-strand of pDAB9582. The actual sequence of the T-strand insert of soybean event pDAB9582.816.15.1 may slightly deviate from SEQ ID NO:14. During the transformation process of introducing an T-stand insert into the genome of plant cells, it is not uncommon for some deletions or other alterations of the insert to occur. Moreover, errors in PCR amplification can occur which might result in minor sequencing errors. For example, flanking sequences listed herein were determined by generating amplicons from soybean genomic DNAs, and then cloning and sequencing the amplicons. It is not unusual to find slight differences and minor discrepancies in sequences generated and determined in this manner, given the many rounds of amplification that are necessary to generate enough amplicon for sequencing from genomic DNAs. One skilled in the art should recognize and be put on notice that any adjustments needed due to these types of common sequencing errors or discrepancies are within the scope of the subject disclosure. Thus, the relevant segment of the plasmid sequence provided herein might comprise some minor variations. Thus, a plant comprising a polynucleotide having some range of identity with the subject insert sequence is within the scope of the subject disclosure. Identity to the sequence of SEQ ID NO:14 can be a polynucleotide sequence having at least 90%, 91%, 92%, 93%, 94%, 95%, 96%, 97%, 98%, 99% sequence identity with a sequence exemplified or described herein. The sequence of the flanking sequences plus insert sequence can be confirmed with reference to the deposited seed. Thus, some differences between SEQ ID NO:14 and the actual T-strand insert of soybean event pDAB9582.816.15.1 may be identified.

Having illustrated and described the principles of the present disclosure, it should be apparent to persons skilled in the art that the disclosure can be modified in arrangement and detail without departing from such principles. We claim all modifications that are within the spirit and scope of the appended claims.

All publications and published patent documents cited in this specification are incorporated herein by reference to the same extent as if each individual publication or patent application was specifically and individually indicated to be incorporated by reference.

The invention claimed is:

1. A soybean plant, or part thereof, that is resistant to *Pseudoplusia includens* (soybean looper) and comprises a DNA sequence comprising SEQ ID NO: 14.

2. A method of controlling insects, said method comprising exposing insects to the insect resistant soybean plant of claim 1, to thereby control the insects.

3. The method of claim 2 wherein said insects are *Pseudoplusia includens* (soybean looper).

4. The method of claim 2 wherein said insects are *Anticarsia gemmatalis* (velvet bean caterpillar).

5. The method of claim 2 wherein said insects are *Spodoptera frugiperda* (fall armyworm).

6. The method of claim 2 wherein said insects are *Heliothis virescens* (tobacco budworm).

7. A method of controlling weeds in a soybean crop, said method comprising applying glufosinate herbicide to the soybean crop, said soybean crop comprising the soybean plants of claim 1.

8. An isolated DNA sequence comprising one or more sequences selected from the group consisting of bp 1258-1288 of SEQ ID NO:1; bp 1223-1323 of SEQ ID NO:1; bp 1173-1373 of SEQ ID NO:1; bp 1073-1473 of SEQ ID NO:1; bp 160-190 of SEQ ID NO:2; bp 125-225 of SEQ ID NO:2; and bp 75-275 of SEQ ID NO:2.

9. A method of breeding the soybean plant of claim 1 comprising:
crossing a first soybean plant with a second soybean plant to produce a third soybean plant, said first soybean plant comprising DNA comprising one or more sequence selected from the group consisting of 1258-1288 of SEQ ID NO:1; bp 1223-1323 of SEQ ID NO:1; bp 1173-1373 of SEQ ID NO:1; bp 1073-1473 of SEQ ID NO:1; bp 160-190 of SEQ ID NO:2; bp 125-225 of SEQ ID NO:2; and bp 75-275 of SEQ ID NO:2 and complements thereof; and assaying said third soybean plant for presence of DNA comprising one or more sequences selected from the group consisting of 1258-1288 of SEQ ID NO:1; bp 1223-1323 of SEQ ID NO:1; bp 1173-1373 of SEQ ID NO:1; bp 1073-1473 of SEQ ID NO:1; bp 160-190 of SEQ ID NO:2; bp 125-225 of SEQ ID NO:2; and bp 75-275 of SEQ ID NO:2, and complements thereof.

10. An isolated DNA molecule comprising a junction sequence comprising the isolated DNA sequence of claim 8, and complements thereof.

11. A seed of the plant of claim 1, wherein the seed comprises a DNA sequence comprising SEQ ID NO: 14.

12. A composition comprising the soybean plant, or parts thereof, of claim 1, wherein said composition is a commodity product selected from the group consisting of soybean meal, soybean flour, and soybean protein concentrate, and wherein said composition comprises a DNA sequence comprising SEQ ID NO: 14.

13. A method of controlling pests in soybean grain, seed, meal, or flour, wherein the method comprises introducing soybean event 9582.816.15.1 into said grain, seed, meal, or flour as demonstrated by said grain, seed, meal, or flour comprising a DNA sequence comprising SEQ ID NO: 14.

14. A soybean plant grown from the soybean seed of claim 11, wherein the plant comprises a DNA sequence comprising SEQ ID NO: 14.

15. A part of the soybean plant of claim 14, wherein said part is selected from the group consisting of pollen, ovule, flowers, shoots, roots, and leaves, and said part comprises said DNA sequence comprising SEQ ID NO: 14.

16. A composition comprising the soybean plant or a part thereof of claim 14, wherein said composition is a commodity product selected from the group consisting of soybean meal and soybean flour, and wherein said composition comprises a DNA sequence comprising SEQ ID NO: 14.

17. A transgenic soybean plant comprising a DNA sequence having SEQ ID NO:14.

18. The transgenic soybean plant of claim 17 or part thereof comprising soybean event 9582.816.15.1, wherein representative soybean seeds comprising soybean event 9582.816.15.1 have been deposited with American Type Culture Collection under Accession No. PTA-12588.

* * * * *

SEQUENCE LISTING

<160> NUMBER OF SEQ ID NOS: 14

<210> SEQ ID NO 1
<211> LENGTH: 1577
<212> TYPE: DNA
<213> ORGANISM: Glycine max

<400> SEQUENCE: 1

```
atatcgatcc cggagggagt gagtagagag gaaatacact aacactggga tcgcacttct      60
actccaggtt ccgataaaca ataagtaaat aaaatactac tactttatca tagtttaatt     120
aacaaaatta tatatactgg tataaaattt aatactttaa ataatcatgt gatttttat      180
```

| | |
|---|---|
| tatctaatta gtattttaat agtttcatta tatattggtg aaaaattaaa atatcaaata | 240 |
| tttcatttat acgttattat aataatataa tattttaaat atacactata ttaaaaataa | 300 |
| atttatacaa cttgataatt attacattta tgtatcttaa ttaaaataat tagtaaaaga | 360 |
| ataaatttaa attaaatatt tttaataaat agaaagttgt gtgataactt tttttatagt | 420 |
| gtaagaaaaa aggcaaatca acaaagaag ttacacccctt aggatcgaga cacttagagc | 480 |
| atcagtaaca agcaagtcca acgagagacg atcaaccccta gaaattatca tgccataatt | 540 |
| tagcccaaac ttaacaagat aattagtact cctattgcct tctctcgatg aatgcacaaa | 600 |
| ttgaacactc aaatcttcct tcacaaagtc acgaatgctt tcacaattg tgcataacaa | 660 |
| tgatacactt gtggcggatg aattccagac acagaatatt aacatactcc aactcccaag | 720 |
| caattcttaa gccatgcaac agtgtcaata actcagcctt aacaatattt gttgaaccaa | 780 |
| tatcaccata gaaaccatat atctaagacc cattaatgtt acgaagcagc ccaccaaatc | 840 |
| ttgcatgccc aagattcctt tagcaacttc catccacaag ttatgaaaca ctgacatgta | 900 |
| tacggacatt ggacatgaca cggacacgta gatatctgta atgttcaaaa tatagaacgt | 960 |
| agtataggtg ttgtgtcagt gtcagacact aacatggatg cgtatcagac accgaacacg | 1020 |
| gtaagggatt ggagtatccg tgcttcatag tccacaagca aggatgattc aagaacttaa | 1080 |
| gaaacttaaa gtaaaattat tttttgacat atattagtat taaaattttt tattgaggta | 1140 |
| tattagtact aattttttt tattaaaatt tattttttaaa cataattta taataaattt | 1200 |
| ttttggagat atattagtac ttaaaagaaa ttagatcttt tttttttggg gtttaaagtc | 1260 |
| cttgctgctt ggaccagtca gcatcatcac accaaaagtt aggcccgaat agtttgaaat | 1320 |
| tagaaagctc gcaattgagg tctacaggcc aaattcgctc ttagccgtac aatattactc | 1380 |
| accggatcct aaccggtgtg atcatgggcc gcgattaaaa atctcaatta tatttggtct | 1440 |
| aatttagttt ggtattgagt aaaacaaatt cggcgccatg cccgggcaag cggccgcaca | 1500 |
| agtttgtaca aaaaagcagg ctccgcggtg actgactgaa aagcttgtcg acctgcaggt | 1560 |
| caacggatca ggatatt | 1577 |

<210> SEQ ID NO 2
<211> LENGTH: 1687
<212> TYPE: DNA
<213> ORGANISM: Glycine max

<400> SEQUENCE: 2

| | |
|---|---|
| gcacatagac acacacatca tctcattgat gcttggtaat aattgtcatt agattgtttt | 60 |
| tatgcataga tgcactcgaa atcagccaat tttagacaag tatcaaacgg atgtgacttc | 120 |
| agtacattaa aaacgtccgc aatgtgttat taagttgtct aagcgtcaat ttgatttgcg | 180 |
| gtgggcaagg ctctctttca gaaagacagg cggccaaagg aacccaaggt gaggtgggct | 240 |
| atggctctca gttccttgtg gaagcgcttg gtctaaggtg cagaggtgtt agcgggatga | 300 |
| agcaaaagtg tccgattgca atctggttgc cagtagcttg aatacactag acccatgttg | 360 |
| gtggcttgca agtcgtatta tcagtgttcc tgcttccttc aaaagtttga acgatattat | 420 |
| tataaagaga aagagtgttg tggataatct aatgaggctg gaccacgtta ttctcaagat | 480 |
| ctaagcattc catataccccc attgaaagat atgaagaatt atgtcaccat gctccaagtg | 540 |
| cttattaagc tactccagct aactagtatt tgaatcaggc ctcacaacat gtactttcaa | 600 |
| ggtgtcccaa acgcgccaaa cattaccaca gtgccaaaaa gatgtgaaag agttcctcat | 660 |
| cggcaaccccc acaacgatta caattcgcat taggaaggac atgaatcatt ttcatgaaac | 720 |

```
tcttggtggg aagaacattg tgatctatct gccataagaa aaattcacgt tctcaagaag      780
atgaataaat atataacaaa taaaaatata ataatatcaa gttataaata aaatttctat      840
ccctcatgtt tactcgcaag tggggtaaat gtgaaatttt tgttttttt ttttacaata      900 ttttttgttt ccttttttaa tcgtcttaaa aagtcagccg gttttcctat atgtaaaaat      960
gaactgatcc aacggctagt ataactctcc cacggttgga catgtgatgg tctctcaccc     1020
tagccaccgt cccgttacat agcccacaat agctgaagtc cgtcagaaaa cttacaaaag     1080
cggtgcgttt caagggatac aagacatgca gcagccgttg ctctaaaccc taaactaaac     1140
taaaacccta gccagttgtc ggtgatcacc atttgtgtaa aaccgtcatg gcgatgaaaa     1200
ctgcagaaga acacgaagtg ggtatctcct gcttcatttc cgaccttcct ggcttccgcg     1260 gaatttttaaa gcaaaggtct cttcattttc tacattaaaa atcattatta ccttcctcac     1320
tgcacctcct ttgtttaatg atgaagtgca ttattcaaca gtgtcttgtt agtgctgatt     1380
caattgaata tgattcaggt attctgattt tatcgtgaat gaagtggaca gagatggaac     1440
agttgttcaa ttgtcctcgc ttgatgcccc tcaagaggag ccagaggtct aattatccgt     1500
gatcattgat aaattgattt gtgctgtttt tgtttttag tatctaactt tttttgggct      1560
tatttcagag ttttcaggaa aatggaacca acacatccga caatgttgta agttatgcct     1620
ctcagattga atctttcaag tctcttgctg gggactctga tgctgttctt ttggaagaat     1680
ttattaa                                                                1687

<210> SEQ ID NO 3
<211> LENGTH: 12381
<212> TYPE: DNA
<213> ORGANISM: Artificial Sequence
<220> FEATURE:
<223> OTHER INFORMATION: Plasmid sequence of pDAB9582

<400> SEQUENCE: 3
agtcagcatc atcacaccaa aagttaggcc cgaatagttt gaaattagaa agctcgcaat       60
tgaggtctac aggccaaatt cgctcttagc cgtacaatat tactcaccgg atcctaaccg      120
gtgtgatcat gggccgcgat taaaaatctc aattatattt ggtctaattt agtttggtat      180
tgagtaaaac aaaattcggcg ccatgcccgg gcaagcggcc gcacaagttt gtacaaaaaa      240
gcaggctccg cggtgactga ctgaaaagct tgtcgacctg caggtcaacg gatcaggata      300
ttcttgttta agatgttgaa ctctatggag gtttgtatga actgatgatc taggaccgga      360
taagttccct tcttcatagc gaacttattc aaagaatgtt tgtgtatca ttcttgttac       420 attgttatta tgaaaaaat attattggtc attggactga acacgagtgt taaatatgga      480
ccaggcccca aataagatcc attgatatat gaattaaata acaagaataa atcgagtcac     540
caaaccactt gcctttttta acgagacttg ttcaccaact tgatacaaaa gtcattatcc     600
tatgcaaatc aataatcata caaaaatatc caataacact aaaaaattaa aagaaatgga     660
taatttcaca atatgttata cgataaagaa gttactttc caagaaattc actgatttta     720
taagcccact tgcattagat aaatggcaaa aaaaacaaa aaggaaaaga aataaagcac     780
gaagaattct agaaaatacg aaatacgctt caatgcagtg ggacccacgg ttcaattatt     840
gccaattttc agctccaccg tatatttaaa aaataaaacg ataatgctaa aaaatataa      900 atcgtaacga tcgttaaatc tcaacggctg gatcttatga cgaccgttag aaattgtggt     960
tgtcgacgag tcagtaataa acggcgtcaa agtggttgca gccggcacac acgagtcgtg    1020
```

```
tttatcaact caaagcacaa atactttttcc tcaacctaaa aataaggcaa ttagccaaaa    1080
acaactttgc gtgtaaacaa cgctcaatac acgtgtcatt ttattattag ctattgcttc    1140
accgccttag ctttctcgtg acctagtcgt cctcgtcttt tcttcttctt cttctataaa    1200
acaataccca aagcttcttc ttcacaattc agatttcaat ttctcaaaat cttaaaaact    1260
ttctctcaat tctctctacc gtgatcaagg taaatttctg tgttccttat tctctcaaaa    1320
tcttcgattt tgttttcgtt cgatcccaat ttcgtatatg ttctttggtt tagattctgt    1380
taatcttaga tcgaagacga ttttctgggt tgatcgtta gatatcatct taattctcga    1440
ttagggtttc ataaatatca tccgatttgt tcaaataatt tgagttttgt cgaataatta    1500
ctcttcgatt tgtgatttct atctagatct ggtgttagtt tctagtttgt gcgatcgaat    1560
ttgtcgatta atctgagttt ttctgattaa cagagatctc catggagaac aatatccaga    1620
accagtgtgt cccatacaat tgcctcaaca atcctgaagt tgagatcctc aacgaagaga    1680
ggagcactgg acgccttccc cttgacatct ccctctccct cacaaggttc cttttgtctg    1740
agtttgttcc tggtgtgggt gtggcctttg gcctctttga cctcatctgg ggcttcatca    1800
ccccatctga ttggagcctc ttccttctcc agattgaaca attgattgag cagaggattg    1860
agaccccttga aggaacaga gccatcacca cacttcgtgg ccttgctgac agctatgaaa    1920
tctacattga agcactccgt gagtgggaag ccaatcccaa caatgctcaa ctccgtgaag    1980
atgtgaggat tcgctttgcc aacacagatg acgcttgat cacagccatc aacaatttca    2040
ccctcaccag ctttgagatc cctttgctct cagtctatgt tcaagctgca aacctccact    2100
tgagcttgct tagggatgct gtgtccttcg dacaaggttg gggacttgac atagccactg    2160
tcaacaatca ctacaacaga ctcatcaact tgattcatcg ctacaccaaa cattgcttgg    2220
acacctacaa tcaaggattg gagaacctca gaggcaccaa cactcgccaa tgggcaaggt    2280
tcaaccagtt tagaagggat ctcacactca ctgtgcttga catagttgct ctcttcccca    2340
actatgatgt tcgcacctac ccaattcaaa ccagctccca acttacaagg gaaatctaca    2400
cctcctcagt cattgaggac agcccagttt ctgccaacat acccaatggt ttcaaccgtg    2460
ctgagtttgg tgtcagacca ccccatctca tggacttcat gaactccttg tttgtgactg    2520
ccgagactgt taggtcccaa actgtgtggg gaggccacct tgttagctcc cgcaacaccg    2580
ctggcaaccg catcaacttc ccatcctatg gggttttcaa tcctggtgga gccatctgga    2640
ttgcagatga ggacccaagg cctttctaca gaaccttgtc agatcctgtc tttgtcagag    2700
gaggctttgg caatccacac tatgttcttg gtttgagggg agtggctttt cagcagactg    2760
gcaccaatca cacccgcaca ttcagaaaca gcggcaccat tgacagcctt gatgagatcc    2820
cacctcaaga caacagcgga gcaccctgga acgactactc ccatgtgctc aatcatgtca    2880
cctttgtgcg ctggcctggt gagatcagcg gttcagattc ttggagagca ccaatgttct    2940
catggaccca tcgctctgcc acacccacaa acaccattga tccagagaga atcacccaga    3000
ttcccttggt gaaggcacac acacttcagt ctggaaccac agttgtcaga gggcctgggt    3060
tcactggtgg agacattctc agacgcacct ctggagggcc atttgcttac accattgtca    3120
acatcaatgg gcaacttccc cagcgttacc gtgccagaat ccgctatgct tccaccacta    3180
acttgagaat ctatgtcaca gttgctggtg aaaggatctt tgctggtcag ttcaacaaga    3240
caatggacac tggtgatcca ttgacattcc agtcattctc ctatgccacc atcaacactg    3300
cattcacctt tccaatgagc cagtccagct tcacagtggg tgcagatacc ttcagctccg    3360
gcaatgaggt gtacattgac cgctttgagt tgattccagt gactgccaca cttgaggctg    3420
```

```
agtctgactt ggagcgtgct cagaaggccg tgaatgctct cttcacctct tcaaatcaga    3480
ttgggctcaa gacagatgtg actgactacc atatagaccg tgtttccaat cttgttgagt    3540
gcctctctga tgagttctgc ttggatgaga agaaagagtt gtcagagaag gtcaagcacg    3600
ccaagaggct ctctgatgag aggaacttgc ttcaagatcc caacttcaga gggatcaacc    3660
gtcaattgga tcgtggatgg aggggatcaa ctgacataac cattcaagga ggtgacgatg    3720
tgttcaagga gaactatgtc acactcttgg ggacctttga tgagtgctac ccaacatacc    3780
tttaccagaa gatagacgaa agcaagctca aggcctacac aagataccag ttgagaggtt    3840
acattgagga ctctcaagac cttgaaatct acctcatcag atacaacgcc aaacatgaga    3900
cagtcaatgt gcctgggact ggttcactct ggccactttc agccccaagc cccattggca    3960
agtgtgccca tcactcacat cacttctcct tggacataga tgttggctgc actgacttga    4020
atgaggacct tggtgtgtgg gtgatcttca agatcaagac ccaagatggc catgcaaggt    4080
tgggcaatct tgagtttctt gaagagaaac cacttgttgg agaagccctt gccagagtga    4140
agagggctga gaagaaatgg agggacaaga gagagaagtt ggagtgggaa acaaacattg    4200
tgtacaaaga agccaaagaa tcagttgatg ctttgtttgt gaactcccaa tatgataggc    4260
tccaagctga caccaacata gcaatgattc atgctgcaga caaagggtt cacagcattc    4320 gtgaagcata ccttcctgaa ctctcagtga ttcctggggt caatgctgca atctttgaag    4380
agcttgaagg acgcatcttc actgccttct ccttgtatga tgcaaggaat gtcatcaaga    4440
atggtgactt caacaatggc ctttcctgct ggaatgtgaa agggcacgtg gatgttgaag    4500
agcagaacaa tcaccgctct gtccttgttg tccctgagtg ggaagctgaa gtttcacaag    4560
aagttcgtgt ctgccctggt cgtggctaca ttcttcgtgt gactgcttac aaagaaggct    4620
atggagaagg ttgtgtcacc atccacgaga tagagaacaa tactgatgaa ttgaagttca    4680
gcaactgtgt tgaggaagag gtctacccaa acaatactgt cacttgcaat gactacactg    4740
caactcaaga agagtatgag ggcacttaca cttctcgcaa ccgtggctat gatggagcct    4800
atgagagcaa ctcatctgtg cctgctgact atgcttcagc ctatgaagag aaggcataca    4860
ctgatggaag gcgtgacaat ccttgtgaaa gcaacagagg ctatgggac tacacacccc    4920 tcccagctgg ctatgtgacc aaagagttgg agtactttcc tgaaactgac aaggtttgga    4980
ttgagatagg agaaactgaa ggcacattca tagttgactc tgtggagctt ttgctcatgg    5040
aagagtgagt agttagctta atcacctaga gctcggtcac cagcataatt tttattaatg    5100
tactaaatta ctgttttgtt aaatgcaatt ttgctttctc gggattttaa tatcaaaatc    5160
tatttagaaa tacacaatat tttgttgcag gcttgctgga gaatcgatct gctatcataa    5220
aaattacaaa aaaattttat ttgcctcaat tattttagga ttggtattaa ggacgcttaa    5280
attatttgtc gggtcactac gcatcattgt gattgagaag atcagcgata cgaaatattc    5340
gtagtactat cgataattta tttgaaaatt cataagaaaa gcaacgttca tgaattgatg    5400 aaacaata caaagacaga taaagccacg cacatttagg atattggccg agattactga    5460
atattgagta agatcacgga atttctgaca ggagcatgtc ttcaattcag cccaaatggc    5520
agttgaaata ctcaaaccgc cccatatgca ggagcggatc attcattgtt tgtttggttg    5580
cctttgccaa catgggagtc caaggttgcg gccgcgcgcc gaaaacaact ttgtatacaa    5640
aagttgccgc ggtgactgac tgaactaaac ccagaaggta attatccaag atgtagcatc    5700
aagaatccaa tgtttacggg aaaaactatg gaagtattat gtaagctcag caagaagcag    5760
```

```
atcaatatgc ggcacatatg caacctatgt tcaaaaatga agaatgtaca gatacaagat    5820
cctatactgc cagaatacga agaagaatac gtagaaattg aaaaagaaga accaggcgaa    5880
gaaaagaatc ttgaagacgt aagcactgac gacaacaatg aaaagaagaa gataaggtcg    5940
gtgattgtga agagacata gaggacacat gtaaggtgga aatgtaagg gcggaaagta     6000 accttatcac aaaggaatct tatcccccac tacttatcct tttatatttt tccgtgtcat    6060
ttttgccctt gagttttcct atataaggaa ccaagttcgg catttgtgaa aacaagaaaa    6120
aatttggtgt aagctatttt ctttgaagta ctgaggatac aacttcagag aaatttgtaa    6180
gtttgtagat ccaacaatgg acaacaatcc caacatcaac gagtgcattc cttacaactg    6240
cctgagcaac cctgaggttg aggtgctggg tggagaacgg attgagactg gttacacacc    6300
tatcgacatc tcgttgtcac ttacccaatt ccttttgtca gagttcgtgc ccggtgctgg    6360
attcgtgctt ggacttgtcg atatcatttg gggaatcttt ggtccctctc aatgggacgc    6420
ctttcttgta cagatagagc agttaattaa ccaaagaata aagaattcg ctaggaacca     6480 agccatctca aggttagaag gcctcagcaa ccttaccag atttacgcag aatcttttcg      6540
agagtgggaa gcagacccga ccaatcctgc cttaagagag gagatgcgca ttcaattcaa    6600
tgacatgaac agcgcgctga cgaccgcaat tccgctcttc gccgttcaga attaccaagt    6660
tcctctttta tccgtgtacg tgcaggctgc caacctgcac ttgtcggtgc tccgcgatgt    6720
ctccgtgttc ggacaacggt ggggctttga tgccgcaact atcaatagtc gttataatga    6780
tctgactagg cttattggca actataccga ttatgctgtt cgctggtaca cacgggtct     6840 cgaacgtgtc tggggaccgg attctagaga ttgggtcagg tacaaccagt tcaggcgaga    6900
gttgacacta actgtcctag acattgtcgc tctcttccc aactacgact ctaggcgcta     6960
cccaatccgt actgtgtcac aattgacccg ggaaatctac acaaaccag tcctcgagaa     7020 cttcgacggt agctttcgag gctcggctca gggcatagag agaagcatca ggtctccaca    7080
cctgatggac atattgaaca gtatcacgat ctacaccgat gcgcaccgcg ttattacta     7140 ctggtcaggg catcagatca tggcatcacc cgttgggttc tctggaccag aattcacttt    7200
cccactttac gggactatgg gcaatgcagc tccacaacaa cgtattgttg ctcaactcgg    7260
tcagggcgtg tatagaacct tgtccagcac tctatatagg agacctttca acatcggcat    7320
caacaatcaa caattgtctg tgcttgacgg gacagaattt gcctatggaa cctcctcaaa    7380
tctgccatcc gctgtctaca gaaagagcgg aacagttgat agcttggatg agatccctcc    7440
acagaacaac aacgttccac ctaggcaagg gtttagccat cgccttagcc atgtgtccat    7500
gttccgttca ggctttagta atagcagcgt tagtatcatc agagctccga tgttctcttg    7560
gatacatcgt agtgctgagt ttaacaacat aattgcatcc gatagcatta ctcagatccc    7620
agctgtcaag gggaactttc tctttaatgg ttctgtcatt tcaggaccag gattcactgg    7680
aggcgacttg gttaggctga attcttccgg caacaacatc cagaatagag ggtatattga    7740
agtgcccatt cacttcccat cgacatctac cagatatcgt gttcgtgtaa ggtatgcctc    7800
tgttacccct attcacctca acgtcaattg gggtaattcc tccatctttt ccaatacagt    7860
accagcgaca gctacatcct tggataatct ccaatctagc gatttcggtt acttcgaaag    7920
tgccaatgcc ttcacctctt ccctaggtaa catagtaggt gttagaaatt tctccggaac    7980
cgccggagtg ataatcgacc gcttcgaatt cattcccgtt actgcaacgc tcgaggcaga    8040
gtctgacttg gaaagagcac agaaggcggt gaatgctctg ttcacttcgt ccaatcagat    8100
tgggctcaag acagatgtga ctgactatca catcgatcgc gttccaacc ttgttgagtg      8160
```

```
cctctctgat gagttctgtt tggatgagaa gaaggagttg tccgagaagg tcaaacatgc   8220
taagcgactt agtgatgagc ggaacttgct tcaagatccc aactttcgcg ggatcaacag   8280
gcaactagat cgtggatgga ggggaagtac ggacatcacc attcaaggag gtgatgatgt   8340
gttcaaggag aactatgtta cgctcttggg tacctttgat gagtgctatc caacatacct   8400
gtaccagaag atagatgaat cgaaactcaa agcctacaca agataccagt tgagaggtta   8460
catcgaggac agtcaagacc ttgagatcta cctcatcaga tacaacgcca aacatgagac   8520
agtcaatgtg cctgggacgg gttcactctg gccactttca gccccaagtc ccatcggcaa   8580
gtgtgcccat cactcacacc acttctcctt ggacatagac gttggctgta ccgacctgaa   8640
cgaagacctc ggtgtgtggg tgatcttcaa gatcaagact caagatggcc atgccaggct   8700
aggcaatctg gagtttctag aagagaaacc acttgttgga gaagccctcg ctagagtgaa   8760
gagggctgag aagaagtgga gggacaagag agagaagttg gaatgggaaa caaacattgt   8820
gtacaaagaa gccaaagaaa gcgttgacgc tctgtttgtg aactctcagt atgataggct   8880
ccaagctgat accaacatag ctatgattca tgctgcagac aaacgcgttc atagcattcg   8940
ggaagcttac cttcctgaac ttagcgtgat tccgggtgtc aatgctgcta tctttgaaga   9000
gttagaaggg cgcatcttca ctgcattctc cttgtatgat gcgaggaatg tcatcaagaa   9060
tggtgacttc aacaatggcc tatcctgctg gaatgtgaaa gggcacgtag atgtagaaga   9120
acagaacaat caccgctctg tccttgttgt tcctgagtgg gaagcagaag tttcacaaga   9180
agttcgtgtc tgtcctggtc gtggctacat tcttcgtgtt accgcgtaca agaaggata   9240 cggagaaggt tgcgtcacca tacacgagat tgagaacaac accgacgagc tgaagttcag   9300
caactgcgtc gaggaggaag tctacccaaa caacaccgta acttgcaatg actcactgc   9360 gactcaagag gagtatgagg gtacttacac ttctcgcaat cgaggatacg atggagccta   9420
tgagagcaac tcttctgtac ccgctgacta tgcatcagcc tatgaggaga aggcttacac   9480
cgatggacgt agggacaatc cttgcgaatc taacagaggc tatggggact acacaccgtt   9540
accagccggc tatgtcacca aagagttaga gtactttcca gaaaccgaca aggtttggat   9600
tgagattgga gaaacggaag gaacattcat tgttgatagc gtggagttac ttctgatgga   9660
ggaatgagta gttagcttaa tcacctagag ctcggttacc tatcaaaatc tatttagaaa   9720
tacacaatat tttgttgcag gcttgctgga gaatcgatct gctatcataa aaattacaaa   9780
aaaattttat ttgcctcaat tattttagga ttggtattaa ggacgcttaa attatttgtc   9840
gggtcactac gcatcattgt gattgagaag atcagcgata cgaaatattc gtagtactat   9900
cgataattta tttgaaaatt cataagaaaa gcaaacgtta catgaattga tgaaacaata   9960
caaagacaga taaagccacg cacatttagg atattggccg agattactga atattgagta  10020
agatcacgga atttctgaca ggagcatgtc ttcaattcag cccaaatggc agttgaaata  10080
ctcaaaccgc cccatatgca ggagcggatc attcattgtt tgtttggttg cctttgccaa  10140
catgggagtc caaggttgcg gccgcgcgcc gacccagctt tcttgtacaa agtggttgcg  10200
gccgcttaat taaatttaaa tgcccgggcg tttaaacgcg gccgcttaat taaggccggc  10260
ctgcagcaaa cccagaaggt aattatccaa gatgtagcat caagaatcca atgtttacgg  10320
gaaaaactat ggaagtatta tgtaagctca gcaagaagca gatcaatatg cggcacatat  10380
gcaacctatg ttcaaaaatg aagaatgtac agatacaaga tcctatactg ccagaatacg  10440
aagaagaata cgtagaaatt gaaaagaag aaccaggcga agaaaagaat cttgaagacg  10500
```

-continued

```
taagcactga cgacaacaat gaaaagaaga agataaggtc ggtgattgtg aaagagacat    10560
agaggacaca tgtaaggtgg aaaatgtaag ggcggaaagt aaccttatca caaaggaatc    10620
ttatccccca ctacttatcc ttttatattt ttccgtgtca tttttgccct tgagttttcc    10680
tatataagga accaagttcg gcatttgtga aaacaagaaa aaatttggtg taagctattt    10740
tctttgaagt actgaggata caacttcaga gaaatttgta agtttgtaga tctccatgtc    10800
tccggagagg agaccagttg agattaggcc agctacagca gctgatatgg ccgcggtttg    10860
tgatatcgtt aaccattaca ttgagacgtc tacagtgaac tttaggacag agccacaaac    10920
accacaagag tggattgatg atctagagag gttgcaagat agatacccct tggttggttgc    10980 tgaggttgag ggtgttgtgg ctggtattgc ttacgctggg ccctggaagg ctaggaacgc    11040
ttacgattgg acagttgaga gtactgttta cgtgtcacat aggcatcaaa ggtttgggcct    11100 aggatccaca ttgtacacac atttgcttaa gtctatggag gcgcaaggtt ttaagtctgt    11160
ggttgctgtt ataggccttc caaacgatcc atctgttagg ttgcatgagg ctttgggata    11220
cacagcccgg ggtacattgc gcgcagctgg atacaagcat ggtggatggc atgatgttgg    11280
tttttggcaa agggattttg agttgccagc tcctccaagg ccagttaggc cagttaccca    11340
gatctgaggt accctgagct tgagcttatg agcttatgag cttagagctc ggatccacta    11400
gtaacggccg ccagtgtgct ggaattcgcc cttgactaga taggcgccca gatcggcggc    11460
aatagcttct tagcgccatc ccgggttgat cctatctgtg ttgaaatagt tgcggtgggc    11520
aaggctctct ttcagaaaga caggcggcca aaggaaccca aggtgaggtg ggctatggct    11580
ctcagttcct tgtggaagcg cttggtctaa ggtgcagagg tgttagcggg atgaagcaaa    11640
agtgtccgat tgtaacaaga tatgttgatc ctacgtaagg atattaaagt atgtattcat    11700
cactaatata atcagtgtat tccaatatgt actacgattt ccaatgtctt tatttgtcgcc    11760 gtatgtaatc ggcgtcacaa aataatcccc ggtgactttc ttttaatcca ggatgaaata    11820
atatgttatt ataattttg cgatttggtc cgttatagga attgaagtgt gcttgcggtc    11880
gccaccactc ccatttcata atttacatg tatttgaaaa ataaaatttt atggtattca    11940
atttaaacac gtatacttgt aaagaatgat atcttgaaag aaatatagtt taaatattta    12000
ttgataaaat aacaagtcag gtattatagt ccaagcaaaa acataaattt attgatgcaa    12060
gtttaaattc agaaatattt caataactga ttatatcagc tggtacattg ccgtagatga    12120
aagactgagt gcgatattat ggtgtaatac atagcggccg ggtttctagt caccggttag    12180
gatccgttta aactcgaggc tagcgcatgc acatagacac acacatcatc tcattgatgc    12240
ttggtaataa ttgtcattag attgttttta tgcatagatg cactcgaaat cagccaattt    12300
tagacaagta tcaaacggat gtgacttcag tacattaaaa acgtccgcaa tgtgttatta    12360
agttgtctaa gcgtcaattt g                                              12381
```

<210> SEQ ID NO 4
<211> LENGTH: 30
<212> TYPE: DNA
<213> ORGANISM: Artificial Sequence
<220> FEATURE:
<223> OTHER INFORMATION: 81615_FW2 primer
<400> SEQUENCE: 4 ttacacccttt aggatcgaga cacttagagc                                      30

<210> SEQ ID NO 5
<211> LENGTH: 27

```
<212> TYPE: DNA
<213> ORGANISM: Artificial Sequence
<220> FEATURE:
<223> OTHER INFORMATION: 81516_RV1 primer

<400> SEQUENCE: 5
gattcatgtc cttcctaatg cgaattg                                     27

<210> SEQ ID NO 6
<211> LENGTH: 25
<212> TYPE: DNA
<213> ORGANISM: Artificial Sequence
<220> FEATURE:
<223> OTHER INFORMATION: 81516_RV2 primer

<400> SEQUENCE: 6
aatttcacat ttaccccact tgcga                                       25

<210> SEQ ID NO 7
<211> LENGTH: 28
<212> TYPE: DNA
<213> ORGANISM: Artificial Sequence
<220> FEATURE:
<223> OTHER INFORMATION: 81516_RV3 primer

<400> SEQUENCE: 7
ggaggtgcag tgaggaaggt aataatga                                    28

<210> SEQ ID NO 8
<211> LENGTH: 29
<212> TYPE: DNA
<213> ORGANISM: Artificial Sequence
<220> FEATURE:
<223> OTHER INFORMATION: 5'IREnd-01 primer

<400> SEQUENCE: 8
cgagctttct aatttcaaac tattcgggc                                   29

<210> SEQ ID NO 9
<211> LENGTH: 30
<212> TYPE: DNA
<213> ORGANISM: Artificial Sequence
<220> FEATURE:
<223> OTHER INFORMATION: 5'IREnd-01 primer

<400> SEQUENCE: 9
tcctagatca tcagttcata caaacctcca                                  30

<210> SEQ ID NO 10
<211> LENGTH: 29
<212> TYPE: DNA
<213> ORGANISM: Artificial Sequence
<220> FEATURE:
<223> OTHER INFORMATION: AtUbi10RV1 primer

<400> SEQUENCE: 10
cggtcctaga tcatcagttc atacaaacc                                   29

<210> SEQ ID NO 11
<211> LENGTH: 28
<212> TYPE: DNA
<213> ORGANISM: Artificial Sequence
<220> FEATURE:
<223> OTHER INFORMATION: AtUbi10RV2 primer

<400> SEQUENCE: 11
```

```
cactcgtgtt cagtccaatg accaataa                                    28

<210> SEQ ID NO 12
<211> LENGTH: 20
<212> TYPE: DNA
<213> ORGANISM: Artificial Sequence
<220> FEATURE:
<223> OTHER INFORMATION: 3'PATEnd05 primer

<400> SEQUENCE: 12
gctcctccaa ggccagttag                                             20

<210> SEQ ID NO 13
<211> LENGTH: 20
<212> TYPE: DNA
<213> ORGANISM: Artificial Sequence
<220> FEATURE:
<223> OTHER INFORMATION: 3'PATEnd06 primer

<400> SEQUENCE: 13
ccagttaggc cagttaccca                                             20

<210> SEQ ID NO 14
<211> LENGTH: 15170
<212> TYPE: DNA
<213> ORGANISM: Artificial Sequence
<220> FEATURE:
<223> OTHER INFORMATION: Expected sequence of soybean event
      9582.814.19.1

<400> SEQUENCE: 14
atatcgatcc cggagggagt gagtagagag gaaatacact aacactggga tcgcacttct     60
actccaggtt ccgataaaca ataagtaaat aaaatactac tactttatca tagtttaatt    120
aacaaaatta tatatactgg tataaaattt aatactttaa ataatcatgt gattttttat    180
tatctaatta gtattttaat agtttcatta tatattggtg aaaaattaaa atatcaaata    240
tttcatttat acgttattat aataatataa tattttaaat atacactata ttaaaaataa    300
atttatacaa cttgataatt attacattta tgtatcttaa ttaaaataat tagtaaaaga    360
ataaatttaa attaaatatt tttaataaat agaaagttgt gtgataactt ttttttatagt    420 gtaagaaaaa aggcaaatca aacaaagaag ttacacccctt aggatcgaga cacttagagc    480
atcagtaaca agcaagtcca acgagagacg atcaacccta gaaattatca tgccataatt    540
tagcccaaac ttaacaagat aattagtact cctattgcct tctctcgatg aatgcacaaa    600
ttgaacactc aaatcttcct tcacaaagtc acgaatgctt tcacaattg tgcataacaa    660 tgatacactt gtggcggatg aattccagac acagaatatt aacatactcc aactcccaag    720
caattcttaa gccatgcaac agtgtcaata actcagcctt aacaatattt gttgaaccaa    780
tatcaccata gaaaccatat atctaagacc cattaatgtt acgaagcagc ccaccaaatc    840
ttgcatgccc aagattcctt tagcaacttc catccacaag ttatgaaaca ctgacatgta    900
tacggacatt ggacatgaca cggacacgta gatatctgta atgttcaaaa tatagaacgt    960
agtataggtg ttgtgtcagt gtcagacact aacatggatg cgtatcagac accgaacacg   1020
gtaagggatt ggagtatccg tgcttcatag tccacaagca aggatgattc aagaacttaa   1080
gaaacttaaa gtaaaattat ttttgacat atattagtat taaaatttt tattgaggta   1140 tattagtact aatttttttt tattaaaatt tattttttaaa cataattttta taataaattt   1200 ttttggagat atattagtac ttaaaagaaa ttagatcttt tttttttggg gtttaaagtc   1260
```

-continued

```
cttgctgctt ggaccagtca gcatcatcac accaaaagtt aggcccgaat agtttgaaat    1320
tagaaagctc gcaattgagg tctacaggcc aaattcgctc ttagccgtac aatattactc    1380
accggatcct aaccggtgtg atcatgggcc gcgattaaaa atctcaatta tatttggtct    1440
aatttagttt ggtattgagt aaaacaaatt cggcgccatg cccgggcaag cggccgcaca    1500
agtttgtaca aaaaagcagg ctccgcggtg actgactgaa aagcttgtcg acctgcaggt    1560
caacggatca ggatattctt gtttaagatg ttgaactcta tggaggtttg tatgaactga    1620
tgatctagga ccggataagt tcccttcttc atagcgaact tattcaaaga atgttttgtg    1680
tatcattctt gttacattgt tattaatgaa aaaatattat tggtcattgg actgaacacg    1740
agtgttaaat atggaccagg ccccaaataa gatccattga tatatgaatt aaataacaag    1800
aataaatcga gtcaccaaac cacttgcctt ttttaacgag acttgttcac caacttgata    1860
caaaagtcat tatcctatgc aaatcaataa tcatacaaaa atatccaata acactaaaaa    1920
attaaaagaa atggataatt tcacaatatg ttatacgata aagaagttac ttttccaaga    1980
aattcactga ttttataagc ccacttgcat tagataaatg gcaaaaaaaa acaaaaagga    2040
aaagaaataa agcacgaaga attctagaaa atacgaaata cgcttcaatg cagtgggacc    2100
cacggttcaa ttattgccaa ttttcagctc caccgtatat ttaaaaaata aaacgataat    2160
gctaaaaaaa tataaatcgt aacgatcgtt aaatctcaac ggctggatct tatgacgacc    2220
gttagaaatt gtggttgtcg acgagtcagt aataaacggc gtcaaagtgg ttgcagccgg    2280
cacacacgag tcgtgtttat caactcaaag cacaaatact tttcctcaac ctaaaaataa    2340
ggcaattagc caaaaacaac tttgcgtgta acaacgctc aatacacgtg tcattttatt    2400
attagctatt gcttcaccgc cttagctttc tcgtgaccta gtcgtcctcg tcttttcttc    2460
ttcttcttct ataaaacaat acccaaagct tcttcttcac aattcagatt tcaatttctc    2520
aaaatcttaa aaactttctc tcaattctct ctaccgtgat caaggtaaat ttctgtgttc    2580
cttattctct caaaatcttc gattttgttt tcgttcgatc ccaatttcgt atatgttctt    2640
tggtttagat tctgttaatc ttagatcgaa gacgattttc tgggtttgat cgttagatat    2700
catcttaatt ctcgattagg gtttcataaa tatcatccga tttgttcaaa taatttgagt    2760
tttgtcgaat aattactctt cgatttgtga tttctatcta gatctggtgt agtttctag    2820 tttgtgcgat cgaatttgtc gattaatctg agttttctg attaacagag atctccatgg    2880
agaacaatat ccagaaccag tgtgtcccat acaattgcct caacaatcct gaagttgaga    2940
tcctcaacga agagaggagc actggacgcc ttccccttga catctccctc tccctcacaa    3000 ggttccttt gtctgagttt gttcctggtg tgggtgtggc ctttggcctc tttgacctca    3060 tctgggctt catcaccca tctgattgga gcctcttcct tctccagatt gaacaattga    3120
ttgagcagag gattgagacc cttgaaagga acagagccat caccacactt cgtggccttg    3180 ctgcagcta tgaaatctac attgaagcac tccgtgagtg ggaagccaat cccaacaatg    3240
ctcaactccg tgaagatgtg aggattcgct ttgccaacac agatgacgct ttgatcacag    3300
ccatcaacaa tttcacccctc accagctttg agatcccttt gctctcagtc tatgttcaag    3360
ctgcaaacct ccacttgagc ttgcttaggg atgctgtgtc cttcggacaa ggttggggac    3420
ttgacatagc cactgtcaac aatcactaca acagactcat caacttgatt catcgctaca    3480
ccaaacattg cttggacacc tacaatcaag gattggagaa cctcagaggc accaacactc    3540
gccaatgggc aaggttcaac cagtttagaa gggatctcac actcactgtg cttgacatag    3600
ttgctctctt ccccaactat gatgttcgca cctacccaat tcaaaccagc tcccaactta    3660
```

-continued

```
caagggaaat ctacacctcc tcagtcattg aggacagccc agtttctgcc aacataccca    3720
atggtttcaa ccgtgctgag tttggtgtca gaccacccca tctcatggac ttcatgaact    3780
ccttgtttgt gactgccgag actgttaggt cccaaactgt gtggggaggc caccttgtta    3840
gctcccgcaa caccgctggc aaccgcatca acttcccatc ctatgggtt ttcaatcctg     3900
gtggagccat ctggattgca gatgaggacc caaggccttt ctacagaacc ttgtcagatc    3960
ctgtctttgt cagaggaggc tttggcaatc cacactatgt tcttggtttg aggggagtgg    4020
cttttcagca gactggcacc aatcacaccc gcacattcag aaacagcggc accattgaca    4080
gccttgatga gatcccacct caagacaaca gcggagcacc ctggaacgac tactcccatg    4140
tgctcaatca tgtcaccttt gtgcgctggc ctggtgagat cagcggttca gattcttgga    4200
gagcaccaat gttctcatgg acccatcgct ctgccacacc cacaaacacc attgatccag    4260
agagaatcac ccagattccc ttggtgaagg cacacacact tcagtctgga accacagttg    4320
tcagagggcc tggttcact ggtggagaca ttctcagacg cacctctgga gggccatttg     4380
cttacaccat tgtcaacatc aatgggcaac ttccccagcg ttaccgtgcc agaatccgct    4440
atgcttccac cactaacttg agaatctatg tcacagttgc tggtgaaagg atctttgctg    4500
gtcagttcaa caagacaatg gacactggtg atccattgac attccagtca ttctcctatg    4560
ccaccatcaa cactgcattc accttttccaa tgagccagtc cagcttcaca gtgggtgcag    4620
ataccttcag ctccggcaat gaggtgtaca ttgaccgctt tgagttgatt ccagtgactg    4680
ccacacttga ggctgagtct gacttggagc gtgctcagaa ggccgtgaat gctctcttca    4740
cctcttcaaa tcagattggg ctcaagacag atgtgactga ctaccatata gaccgtgttt    4800
ccaatcttgt tgagtgcctc tctgatgagt tctgcttgga tgagaagaaa gagttgtcag    4860
agaaggtcaa gcacgccaag aggctctctg atgagaggaa cttgcttcaa gatcccaact    4920
tcagagggat caaccgtcaa ttggatcgtg gatggagggg atcaactgac ataaccattc    4980
aaggaggtga cgatgtgttc aaggagaact atgtcacact cttggggacc tttgatgagt    5040
gctacccaac atacctttac cagaagatag acgaaagcaa gctcaaggcc tacacaagat    5100
accagttgag aggttacatt gaggactctc aagaccttga atctacctc atcagataca     5160
acgccaaaca tgagacagtc aatgtgcctg ggactggttc actctggcca ctttcagccc    5220
caagcccat tggcaagtgt gcccatcact cacatcactt ctccttggac atagatgttg      5280
gctgcactga cttgaatgag gaccttggtg tgtgggtgat cttcaagatc aagacccaag    5340
atggccatgc aaggttgggc aatcttgagt ttccttgaaga gaaaccactt gttggagaag    5400
cccttgccag agtgaagagg gctgagaaga atggaggga caagagagag aagttggagt     5460
gggaaacaaa cattgtgtac aaagaagcca agaatcagt tgatgctttg tttgtgaact      5520
cccaatatga taggctccaa gctgacacca acatagcaat gattcatgct gcagacaaaa    5580
gggttcacag cattcgtgaa gcataccttc ctgaactctc agtgattcct ggggtcaatg    5640
ctgcaatctt tgaagagctt gaaggacgca tcttcactgc cttctccttg tatgatgcaa    5700
ggaatgtcat caagaatggt gacttcaaca atggcctttc ctgctggaat gtgaagggc     5760
acgtggatgt tgaagagcag aacaatcacc gctctgtcct tgttgtccct gagtgggaag    5820
ctgaagtttc acaagaagtt cgtgtctgcc ctggtcgtgg ctacattctt cgtgtgactg    5880
cttacaaaga aggctatgga gaaggttgtg tcaccatcca cgagatagag aacaatactg    5940
atgaattgaa gttcagcaac tgtgttgagg aagaggtcta cccaaacaat actgtcactt    6000
```

```
gcaatgacta cactgcaact caagaagagt atgagggcac ttacacttct cgcaaccgtg    6060
gctatgatgg agcctatgag agcaactcat ctgtgcctgc tgactatgct tcagcctatg    6120
aagagaaggc atacactgat ggaaggcgtg acaatccttg tgaaagcaac agaggctatg    6180
gggactacac acccctccca gctggctatg tgaccaaaga gttggagtac tttcctgaaa    6240
ctgacaaggt ttggattgag ataggagaaa ctgaaggcac attcatagtt gactctgtgg    6300
agcttttgct catggaagag tgagtagtta gcttaatcac ctagagctcg gtcaccagca    6360 taattttat taatgtacta aattactgtt ttgttaaatg caattttgct ttctcgggat     6420
tttaatatca aaatctattt agaaatacac aatattttgt tgcaggcttg ctggagaatc    6480
gatctgctat cataaaaatt acaaaaaaat tttatttgcc tcaattattt taggattggt    6540
attaaggacg cttaaattat ttgtcgggtc actacgcatc attgtgattg agaagatcag    6600
cgatacgaaa tattcgtagt actatcgata atttatttga aaattcataa gaaaagcaaa    6660
cgttacatga attgatgaaa caatacaaag acagataaag ccacgcacat ttaggatatt    6720
ggccgagatt actgaatatt gagtaagatc acggaatttc tgacaggagc atgtcttcaa    6780
ttcagcccaa atggcagttg aaatactcaa accgccccat atgcaggagc ggatcattca    6840
ttgtttgttt ggttgccttt gccaacatgg gagtccaagg ttgcggccgc gcgccgaaaa    6900
caactttgta tacaaaagtt gccgcggtga ctgactgaac taaacccaga aggtaattat    6960
ccaagatgta gcatcaagaa tccaatgttt acgggaaaaa ctatggaagt attatgtaag    7020
ctcagcaaga agcagatcaa tatgcggcac atatgcaacc tatgttcaaa aatgaagaat    7080
gtacagatac aagatcctat actgccagaa tacgaagaag aatacgtaga aattgaaaaa    7140
gaagaaccag gcgaagaaaa gaatcttgaa gacgtaagca ctgacgacaa caatgaaaag    7200
aagaagataa ggtcggtgat tgtgaaagag acatagagga cacatgtaag gtggaaaatg    7260
taagggcgga aagtaacctt atcacaaagg aatcttatcc cccactactt atccttttat    7320 attttttccgt gtcattttttg ccccttgagtt ttcctatata aggaaccaag ttcggcattt    7380
gtgaaaacaa gaaaaaattt ggtgtaagct attttctttg aagtactgag gatacaactt    7440
cagagaaatt tgtaagtttg tagatccaac aatggacaac aatcccaaca tcaacgagtg    7500
cattccttac aactgcctga gcaaccctga ggttgaggtg ctgggtggag aacggattga    7560
gactggttac acacctatcg acatctcgtt gtcacttacc caattccttt tgtcagagtt    7620
cgtgcccggt gctggattcg tgcttggact tgtcgatatc atttggggaa tctttggtcc    7680
ctctcaatgg gacgcctttc ttgtacagat agagcagtta attaaccaaa gaatagaaga    7740
attcgctagg aaccaagcca tctcaaggtt agaaggcctc agcaaccttt accagattta    7800
cgcagaatct tttcgagagt gggaagcaga cccgaccaat cctgccttaa gagaggagat    7860
gcgcattcaa ttcaatgaca tgaacagcgc gctgacgacc gcaattccgc tcttcgccgt    7920
tcagaattac caagttcctc tttttatccgt gtacgtgcag gctgccaacc tgcacttgtc    7980
ggtgctccgc gatgtctccg tgttcggaca acggtggggc tttgatgccg caactatcaa    8040
tagtcgttat aatgatctga ctaggcttat tggcaactat accgattatg ctgttcgctg    8100
gtacaacacg ggtctcgaac gtgtctgggg accggattct agagattggg tcaggtacaa    8160
ccagttcagg cgagagttga cactaactgt cctagacatt gtcgctctct ttcccaacta    8220
cgactctagg cgctacccaa tccgtactgt gtcacaattg acccgggaaa tctacacaaa    8280
cccagtcctc gagaacttcg acggtagctt tcgaggctcg gctcagggca tagagagaag    8340
catcaggtct ccacacctga tggacatatt gaacagtatc acgatctaca ccgatgcgca    8400
```

```
ccgcggttat tactactggt cagggcatca gatcatggca tcacccgttg ggttctctgg    8460
accagaattc actttcccac tttacgggac tatgggcaat gcagctccac aacaacgtat    8520
tgttgctcaa ctcggtcagg gcgtgtatag aaccttgtcc agcactctat ataggagacc    8580
tttcaacatc ggcatcaaca atcaacaatt gtctgtgctt gacgggacag aatttgccta    8640
tggaacctcc tcaaatctgc catccgctgt ctacagaaag agcggaacag ttgatagctt    8700
ggatgagatc cctccacaga acaacaacgt tccacctagg caagggttta gccatcgcct    8760
tagccatgtg tccatgttcc gttcaggctt tagtaatagc agcgttagta tcatcagagc    8820
tccgatgttc tcttggatac atcgtagtgc tgagtttaac aacataattg catccgatag    8880
cattactcag atcccagctg tcaaggggaa ctttctcttt aatggttctg tcatttcagg    8940
accaggattc actggaggcg acttggttag gctgaattct tccggcaaca acatccagaa    9000
tagagggtat attgaagtgc ccattcactt cccatcgaca tctaccagat atcgtgttcg    9060
tgtaaggtat gcctctgtta cccctattca cctcaacgtc aattggggta attcctccat    9120
cttttccaat acagtaccag cgacagctac atccttggat aatctccaat ctagcgattt    9180
cggttacttc gaaagtgcca atgccttcac ctcttcccta ggtaacatag taggtgttag    9240
aaatttctcc ggaaccgccg gagtgataat cgaccgcttc gaattcattc ccgttactgc    9300
aacgctcgag gcagagtctg acttggaaag agcacagaag gcggtgaatg ctctgttcac    9360
ttcgtccaat cagattgggc tcaagacaga tgtgactgac tatcacatcg atcgcgtttc    9420
caaccttgtt gagtgcctct ctgatgagtt ctgtttggat gagaagaagg agttgtccga    9480
gaaggtcaaa catgctaagc gacttagtga tgagcggaac ttgcttcaag atcccaactt    9540
tcgcgggatc aacaggcaac tagatcgtgg atggagggga agtacggaca tcaccattca    9600
aggaggtgat gatgtgttca aggagaacta tgttacgctc ttgggtacct ttgatgagtg    9660
ctatccaaca tacctgtacc agaagataga tgaatcgaaa ctcaaagcct acacaagata    9720
ccagttgaga ggttacatcg aggacagtca agaccttgag atctacctca tcagatacaa    9780
cgccaaacat gagacagtca atgtgcctgg gacgggttca ctctggccac tttcagcccc    9840
aagtcccatc ggcaagtgtg cccatcactc acaccacttc tccttggaca tagacgttgg    9900
ctgtaccgac ctgaacgaag acctcggtgt gtgggtgatc ttcaagatca agactcaaga    9960
tggccatgcc aggctaggca atctggagtt tctagaagag aaaccacttg ttggagaagc    10020
cctcgctaga gtgaagaggg ctgagaagaa gtggagggac aagagagaga agttggaatg    10080
ggaaacaaac attgtgtaca agaagccaaa agaaagcgtt gacgctctgt ttgtgaactc    10140
tcagtatgat aggctccaag ctgataccaa catagctatg attcatgctg cagacaaacg    10200
cgttcatagc attcgggaag cttaccttcc tgaacttagc gtgattccgg gtgtcaatgc    10260
tgctatcttt gaagagttag aagggcgcat cttcactgca ttctccttgt atgatgcgag    10320
gaatgtcatc aagaatggtg acttcaacaa tggcctatcc tgctggaatg tgaaagggca    10380
cgtagatgta gaagaacaga acaatcaccg ctctgtcctt gttgttcctg agtgggaagc    10440
agaagtttca caagaagttc gtgtctgtcc tggtcgtggc tacattcttc gtgttaccgc    10500
gtacaaagaa ggatacggag aaggttgcgt caccatacac gagattgaga acaacaccga    10560
cgagctgaag ttcagcaact gcgtcgagga ggaagtctac ccaaacaaca ccgtaacttg    10620
caatgactac actgcgactc aagaggagta tgagggtact tacacttctc gcaatcgagg    10680
atacgatgga gcctatgaga gcaactcttc tgtacccgct gactatgcat cagcctatga    10740
```

```
ggagaaggct tacaccgatg gacgtaggga caatccttgc gaatctaaca gaggctatgg  10800
ggactacaca ccgttaccag ccggctatgt caccaaagag ttagagtact ttccagaaac  10860
cgacaaggtt tggattgaga ttggagaaac ggaaggaaca ttcattgttg atagcgtgga  10920
gttacttctg atggaggaat gagtagttag cttaatcacc tagagctcgg ttacctatca  10980
aaatctattt agaaatacac aatattttgt tgcaggcttg ctggagaatc gatctgctat  11040
cataaaaatt acaaaaaaat tttatttgcc tcaattattt taggattggt attaaggacg  11100
cttaaattat ttgtcgggtc actacgcatc attgtgattg agaagatcag cgatacgaaa  11160
tattcgtagt actatcgata atttatttga aaattcataa gaaaagcaaa cgttacatga  11220
attgatgaaa caatacaaag acagataaag ccacgcacat ttaggatatt ggccgagatt  11280
actgaatatt gagtaagatc acggaatttc tgacaggagc atgtcttcaa ttcagcccaa  11340
atggcagttg aaatactcaa accgccccat atgcaggagc ggatcattca ttgtttgttt  11400
ggttgccttt gccaacatgg gagtccaagg ttgcggccgc gcgccgaccc agctttcttg  11460
tacaaagtgg ttgcggccgc ttaattaaat ttaaatgccc gggcgtttaa acgcggccgc  11520
ttaattaagg ccggcctgca gcaaacccag aaggtaatta tccaagatgt agcatcaaga  11580
atccaatgtt tacgggaaaa actatggaag tattatgtaa gctcagcaag aagcagatca  11640
atatgcggca catatgcaac ctatgttcaa aaatgaagaa tgtacagata caagatccta  11700
tactgccaga atacgaagaa gaatacgtag aaattgaaaa agaagaacca ggcgaagaaa  11760
agaatcttga agacgtaagc actgacgaca acaatgaaaa gaagaagata aggtcggtga  11820
ttgtgaaaga gacatagagg acacatgtaa ggtggaaaat gtaagggcgg aaagtaacct  11880
tatcacaaag gaatcttatc ccccactact tatcctttta tattttttccg tgtcattttt  11940 gcccttgagt tttcctatat aaggaaccaa gttcggcatt tgtgaaaaca agaaaaaatt  12000
tggtgtaagc tattttcttt gaagtactga ggatacaact tcagagaaat ttgtaagttt  12060
gtagatctcc atgtctccgg agaggagacc agttgagatt aggccagcta cagcagctga  12120
tatggccgcg gtttgtgata tcgttaacca ttacattgag acgtctacag tgaactttag  12180
gacagagcca caaacaccac aagagtggat tgatgatcta gagaggttgc aagatagata  12240
cccttggttg gttgctgagg ttgagggtgt tgtggctggt attgcttacg ctgggccctg  12300
gaaggctagg aacgcttacg attggacagt tgagagtact gtttacgtgt cacataggca  12360
tcaaaggttg ggcctaggat ccacattgta cacacatttg cttaagtcta tggaggcgca  12420
aggttttaag tctgtggttg ctgttatagg ccttccaaac gatccatctg ttaggttgca  12480
tgaggctttg ggatacacag cccgggggtac attgcgcgca gctggataca agcatggtgg  12540
atggcatgat gttggttttt ggcaaaggga ttttgagttg ccagctcctc caaggccagt  12600
taggccagtt acccagatct gaggtaccct gagcttgagc ttatgagctt atgagcttag  12660
agctcggatc cactagtaac ggccgccagt gtgctggaat tcgcccttga ctagataggc  12720
gcccagatcg gcggcaatag cttcttagcg ccatcccggg ttgatcctat ctgtgttgaa  12780
atagttgcgg tgggcaaggc tctctttcag aaagacaggc ggccaaagga acccaaggtg  12840
aggtgggcta tggctctcag ttccttgtgg aagcgcttgg tctaaggtgc agaggtgtta  12900
gcgggatgaa gcaaaagtgt ccgattgtaa caagatatgt tgatcctacg taaggatatt  12960
aaagtatgta ttcatcacta atataatcag tgtattccaa tatgtactac gatttccaat  13020
gtctttattg tcgccgtatg taatcggcgt cacaaaataa tccccggtga ctttctttta  13080
atccaggatg aaataatatg ttattataat ttttgcgatt tggtccgtta taggaattga  13140
```

```
agtgtgcttg cggtcgccac cactcccatt tcataatttt acatgtattt gaaaaataaa    13200
aatttatggt attcaattta aacacgtata cttgtaaaga atgatatctt gaaagaaata    13260
tagtttaaat atttattgat aaaataacaa gtcaggtatt atagtccaag caaaaacata    13320
aatttattga tgcaagttta aattcagaaa tatttcaata actgattata tcagctggta    13380
cattgccgta gatgaaagac tgagtgcgat attatggtgt aatacatagc ggccgggttt    13440
ctagtcaccg gttaggatcc gtttaaactc gaggctagcg catgcacata gacacacaca    13500
tcatctcatt gatgcttggt aataattgtc attagattgt ttttatgcat agatgcactc    13560
gaaatcagcc aattttagac aagtatcaaa cggatgtgac ttcagtacat taaaaacgtc    13620
cgcaatgtgt tattaagttg tctaagcgtc aatttgattt gcggtgggca aggctctctt    13680
tcagaaagac aggcggccaa aggaacccaa ggtgaggtgg gctatggctc tcagttcctt    13740
gtggaagcgc ttggtctaag gtgcagaggt gttagcggga tgaagcaaaa gtgtccgatt    13800
gcaatctggt tgccagtagc ttgaatacac tagacccatg ttggtggctt gcaagtcgta    13860
ttatcagtgt tcctgcttcc ttcaaaagtt tgaacgatat tattataaag agaaagagtg    13920
ttgtggataa tctaatgagg ctggaccacg ttattctcaa gatctaagca ttccatatac    13980
cccattgaaa gatatgaaga attatgtcac catgctccaa gtgcttatta agctactcca    14040
gctaactagt atttgaatca ggcctcacaa catgtacttt caaggtgtcc caaacgcgcc    14100
aaacattacc acagtgccaa aaagatgtga aagagttcct catcggcaac cccacaacga    14160
ttacaattcg cattaggaag gacatgaatc attttcatga aactcttggt gggaagaaca    14220
ttgtgatcta tctgccataa gaaaaattca cgttctcaag aagatgaata aatatataac    14280
aaataaaaat ataataatat caagttataa ataaaatttc tatccctcat gtttactcgc    14340
aagtggggta aatgtgaaat ttttgttttt ttttttttaca atattttttg tttccttttt    14400
taatcgtctt aaaaagtcag ccggttttcc tatatgtaaa aatgaactga tccaacggct    14460
agtataactc tcccacggtt ggacatgtga tggtctctca ccctagccac cgtcccgtta    14520
catagcccac aatagctgaa gtccgtcaga aaacttacaa aagcggtgcg tttcaaggga    14580
tacaagacat gcagcagccg ttgctctaaa ccctaaacta aactaaaacc ctagccagtt    14640
gtcggtgatc accatttgtg taaaaccgtc atggcgatga aaactgcaga agaacacgaa    14700
gtgggtatct cctgcttcat ttccgacctt cctggcttcc gcggaatttt aaagcaaagg    14760
tctcttcatt ttctacatta aaaatcatta ttaccttcct cactgcacct cctttgttta    14820
atgatgaagt gcattattca acagtgtctt gttagtgctg attcaattga atatgattca    14880
ggtattctga ttttatcgtg aatgaagtgg acagagatgg aacagttgtt caattgtcct    14940
cgcttgatgc ccctcaagag gagccagagg tctaattatc cgtgatcatt gataaattga    15000
tttgtgctgt ttttgttttt tagtatctaa ctttttttgg gcttatttca gagttttcag    15060
gaaaatggaa ccaacacatc cgacaatgtt gtaagttatg cctctcagat tgaatctttc    15120
aagtctcttg ctggggactc tgatgctgtt cttttggaag aatttattaa                15170
```